(12) United States Patent
Pierce et al.

(10) Patent No.: US 8,478,543 B2
(45) Date of Patent: Jul. 2, 2013

(54) SYSTEM AND METHOD FOR NUCLEIC ACID SEQUENCE DESIGN

(75) Inventors: Niles A. Pierce, South Pasadena, CA (US); Brian R. Wolfe, Pasadena, CA (US); Joseph Zadeh, San Francisco, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/079,747

(22) Filed: Apr. 4, 2011

(65) Prior Publication Data

US 2011/0288832 A1 Nov. 24, 2011

Related U.S. Application Data

(60) Provisional application No. 61/320,863, filed on Apr. 5, 2010.

(51) Int. Cl.
*G01N 33/48* (2006.01)
*G06F 19/00* (2006.01)

(52) U.S. Cl.
USPC ............................................. 702/19; 702/20

(58) Field of Classification Search
None
See application file for complete search history.

(56) References Cited

U.S. PATENT DOCUMENTS

| 6,128,587 A | 10/2000 | Sjolander |
| 7,727,721 B2 | 6/2010 | Pierce et al. |
| 2008/0183958 A1 | 7/2008 | Cheriton |

FOREIGN PATENT DOCUMENTS

| WO | WO 2007/141809 A1 | 12/2007 |
| WO | WO 2007/148337 A2 | 12/2007 |

OTHER PUBLICATIONS

Hofacker et al., "Fast Folding and Comparison of RNA Secondary Structures," (Monatshefte fur Chemie, Chemical Monthly, vol. 125 (1994) pp. 167-188).*

Andronescu, et al. "A New Algorithm for RNA Secondary Structure Design." Journal of Molecular Biology (online), Feb. 20, 2004 [Retrieved on Jun. 7, 2011), vol. 336, Iss. 3, pp. 607-624, Retrieved from the Internet: <URL: http://http://citeseerx.ist.psu.edu/viewdoc/download?doi=10.1.1.3.46&rep=rep1&type=pdf>.
Zadeh. "Algorithms for nucleic acid sequence design." Doctoral Thesis [online[, orally defended Dec. 8, 2009, published May 25, 2010, [Retrieved on Jun. 7, 2011], pp. 1-85, Retrieved from the Internet: <URL: http://resolver.caltech.edu/CaltechTHESIS:05112010-205335518>.
Zadeh. "Algorithms for nucleic acid sequence design." Doctoral Thesis, defended Dec. 8, 2009; Abstract only [online]; downloaded from URL: http://thesis.library.caltech.edu/5801/ on Jul. 6, 2011.
International Search Report and Written Opinion of the International Searching Authority for PCT/US11/31127, mailed Oct. 31, 2011.
Choi, et al. (2010). Programmable in situ amplification for multiplexed imaging of mRNA expression. *Nature. Biotechnol.*, 28:1208-1212.
Dirks, et al. (2004). Triggered amplification by hybridization chain reaction. *Proc Natl Acad Sci USA*, 101(43):15275-15278.
Venkataraman, et al. (2010). Selective cell death mediated by small conditional RNAs. *Proc Natl Acad Sci USA*, 107(39):16777-16782.
Yin, et al. (2008). Programming biomolecular self-assembly pathways. *Nature*, 451:318-322.

* cited by examiner

*Primary Examiner* — Anna Skibinsky
(74) *Attorney, Agent, or Firm* — Knobbe, Martens, Olson & Bear LLP

(57) ABSTRACT

Described herein are systems and processes for designing the sequence of one or more interacting nucleic acid strands intended to adopt a target secondary structure at equilibrium. The target secondary structure is decomposed into a binary tree and candidate mutations are evaluated on leaf nodes of the tree. During a process of leaf optimization, defect-weighted mutation sampling is used to select each candidate mutation position with a probability proportional to its contribution to an ensemble defect of the leaf. Subsequences of the tree are then merged, moving up the tree until a final nucleotide sequence of interest is determined that has the target secondary structure at equilibrium.

21 Claims, 25 Drawing Sheets

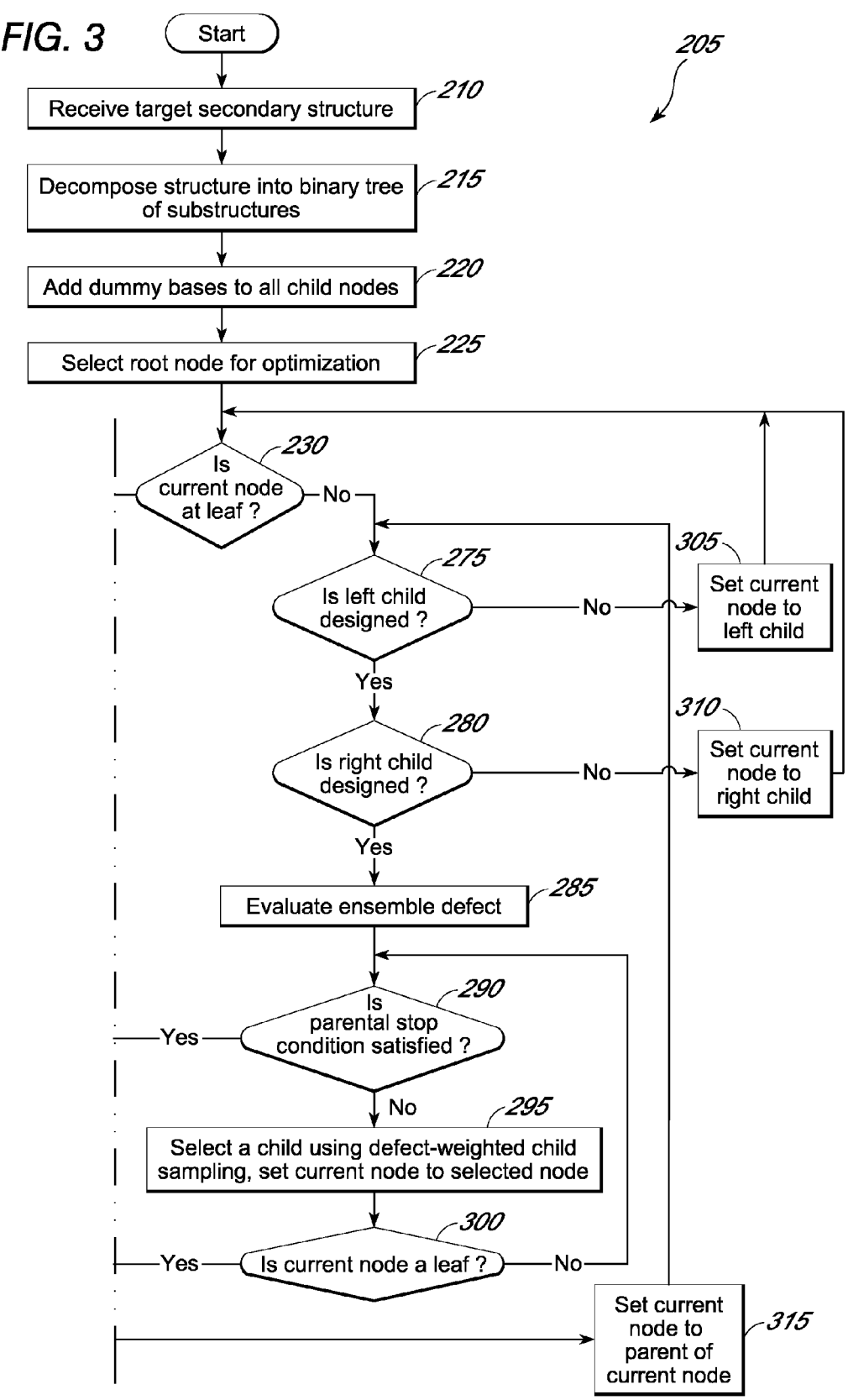

```
DESIGNSEQ(φ, s, n, k)
  a ← DEPTH(k)
  if HASCHILDREN(k)
    m_reopt ← 0
    if n = 0
      ψ_l ← DESIGNSEQ(0, s_l+, 0, k_l)
      φ_r ← DESIGNSEQ(0, s_r+, 0, k_r)
    else
      UPDATECHILDREN(k, a, a − 1)
      child, φ ← WEIGHTEDCHILDSAMPLING(φ, s, n_l, n_r)
      φ_child ← DESIGNSEQ(φ_child+, s_child+, n_child+, k_child)
      n^{k,a} ← ENSEMBLEDEFECT(φ, s)
      UPDATECHILDREN(k, a, a + 1)
      while n^{k,a} > max(f_stop|s_l|, n^{k_l,a}_native) + max(f_stop|s_r|, n^{k_r,a}_native)
        and m_reopt < M_reopt
        child, φ̂ ← WEIGHTEDCHILDSAMPLING(φ, s, n^{k,a}_l, n^{k,a}_r)
        φ̂_child ← DESIGNSEQ(φ_child+, s_child+, n^{k,a}_child+, k_child)
        n̂ ← ENSEMBLEDEFECT(φ̂, s)
        if n̂ < n^{k,a}
          φ, n^{k,a} ← φ̂, n̂
          UPDATECHILDREN(k, a, a, + 1)
        m_reopt ← m_reopt + 1
  else
    m_leafopt ← 0
    φ, n^{k,a} ← OPTIMIZELEAF(s)
    while n^{k,a} > f_stop|s| and m_leafopt < M_leafopt
      φ̂, n̂ ← OPTIMIZELEAF(s)
      if n̂ < n^{k,a}
        φ, n^{k,a} ← φ̂, n̂
      m_leafopt ← m_leafopt + 1
  return φ_native UPDATECHILDREN(k, a, b)
  if HASCHILDREN(k)
    n^{k_l,a} ← n^{k_l,b}
    n^{k_r,a} ← n^{k_r,b}
    UPDATECHILDREN(k_l, a, b)
    UPDATECHILDREN(k_r, a, b)

OPTIMIZELEAF(s)
  m_unfavorable ← 0
  γ_unfavorable ← ∅
  φ ← INITSEQ(s)
  n ← ENSEMBLEDEFECT(φ, s)
  while n > f_stop|s| and m_unfavorable < M_unfavorable|s|
    ξ, φ̂ ← WEIGHTEDMUTATIONSAMPLING(φ, s, n_1, ..., n_|s|)
    if ξ ∈ γ_unfavorable
      m_unfavorable ← m_unfavorable + 1
    else
      n̂ ← ENSEMBLEDEFECT(φ̂, s)
      if n̂ < n
        φ, n ← φ̂, n̂
        m_unfavorable ← 0
        γ_unfavorable ← ∅
      else
        m_unfavorable ← m_unfavorable + 1
        γ_unfavorable ← γ_unfavorable ∪ ξ
  return φ, n
```

FIG. 4

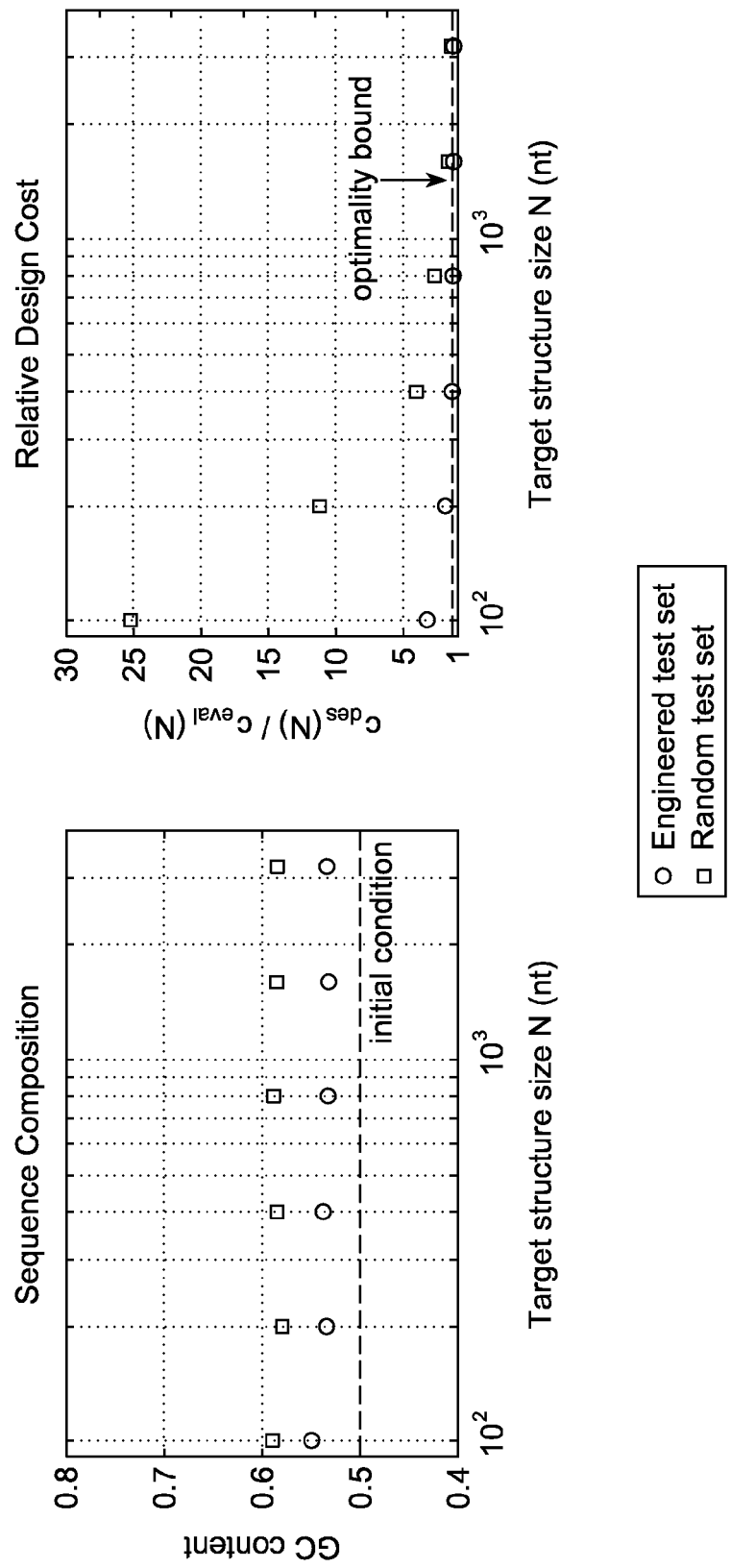

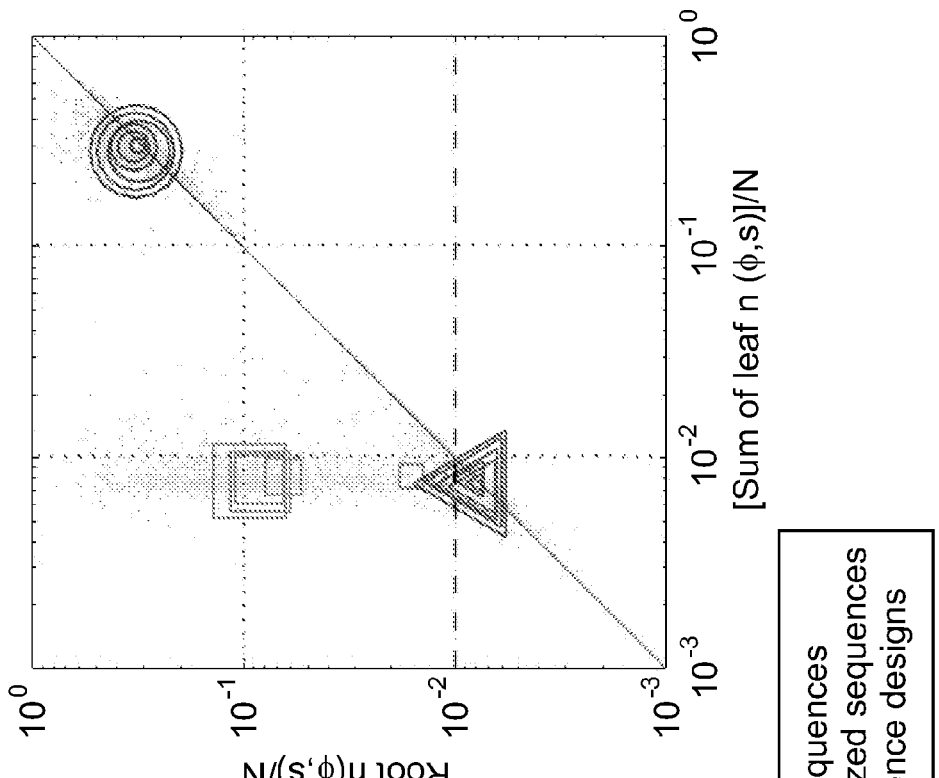
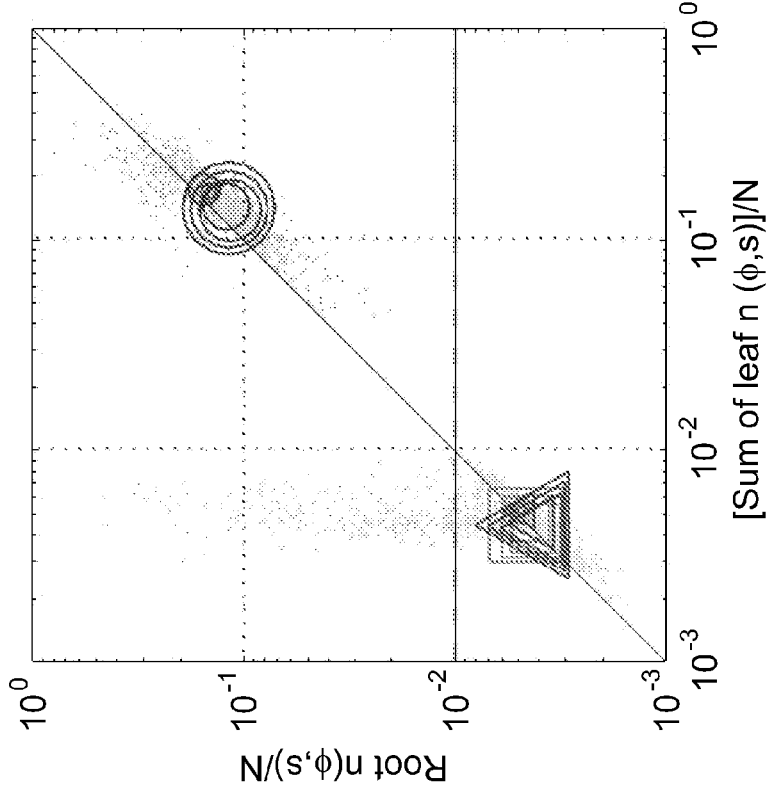
FIG. 7A
FIG. 7B
○ Random sequences
□ Leaf-optimized sequences
△ Final sequence designs

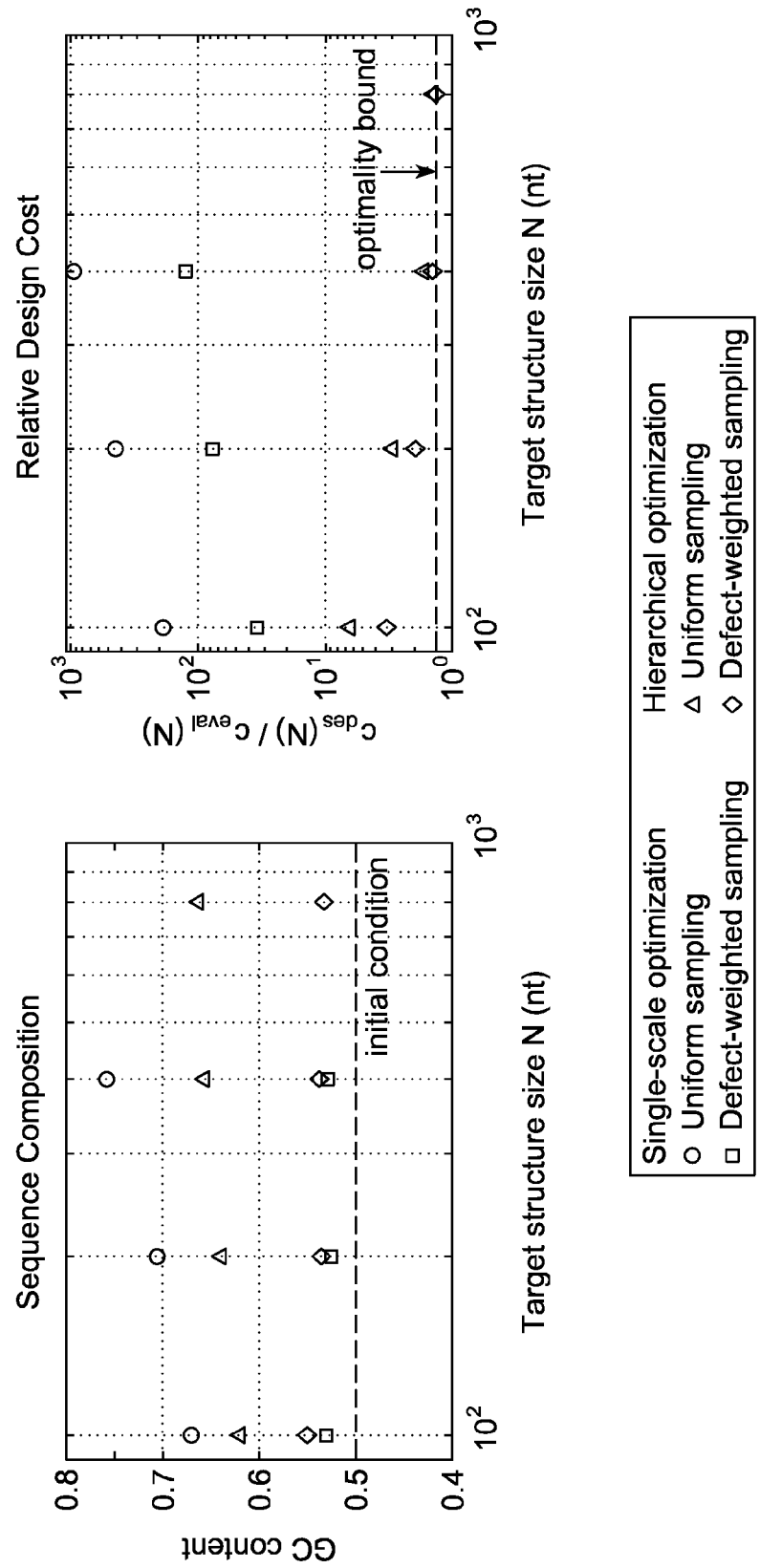

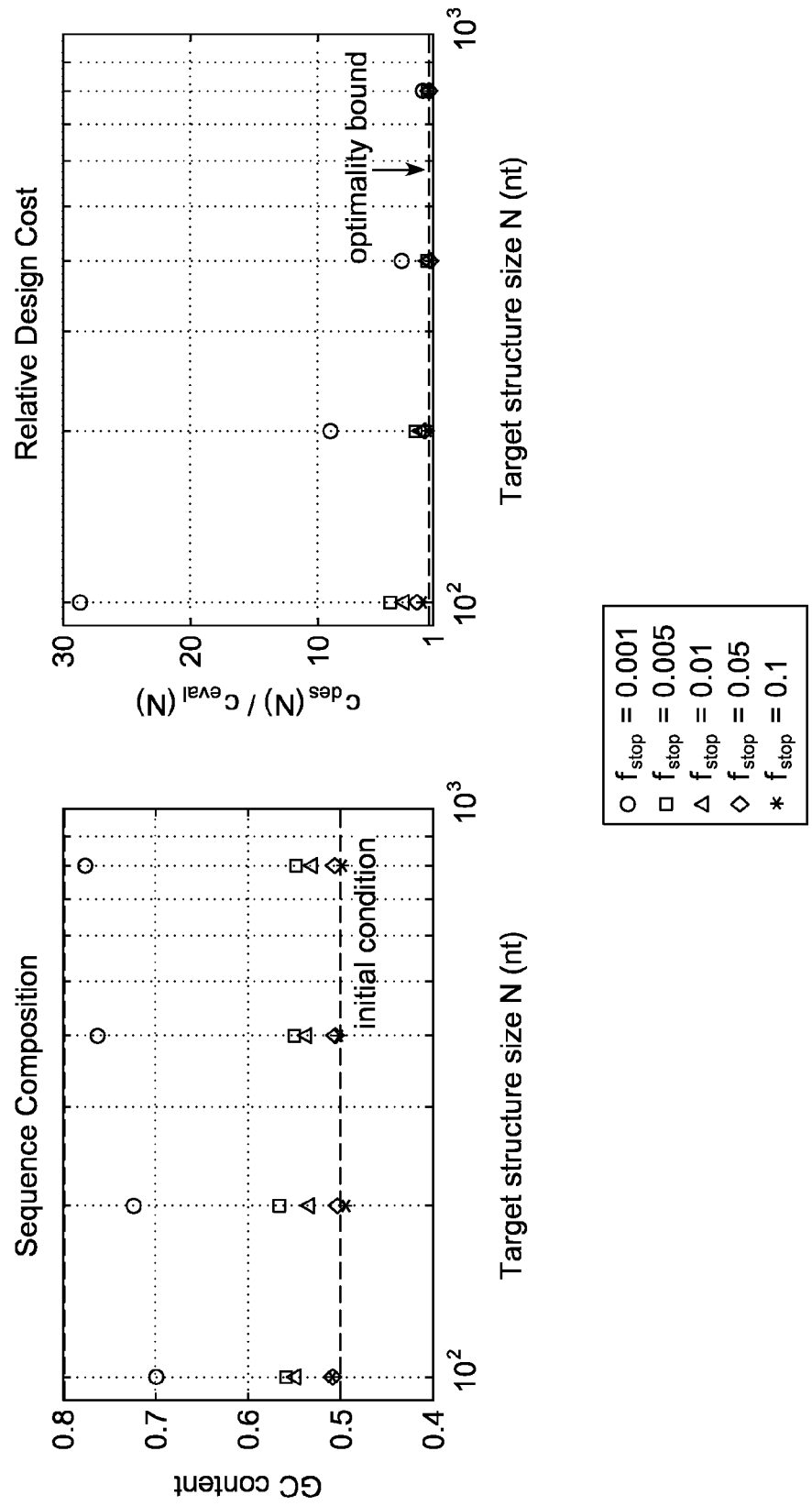

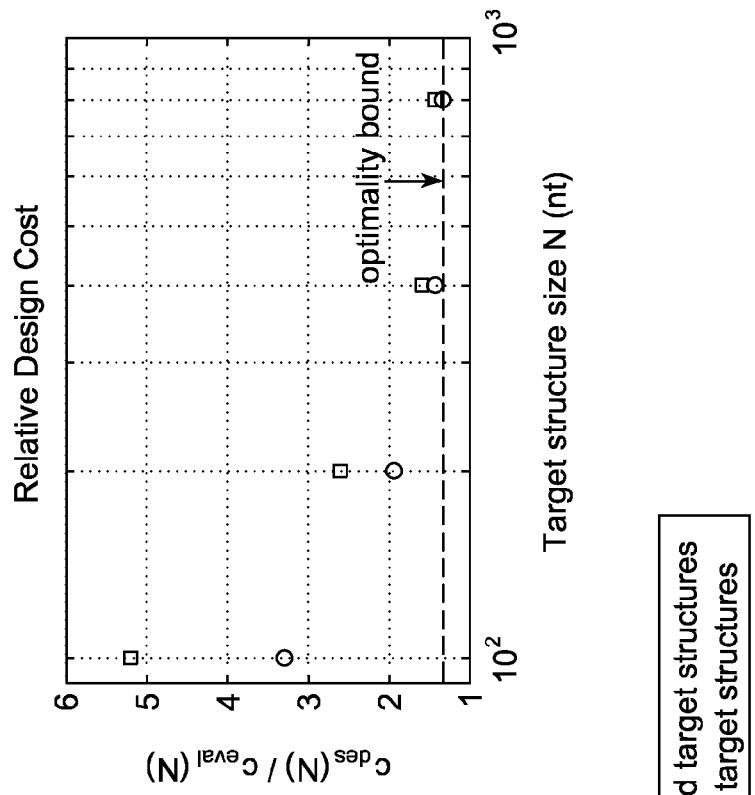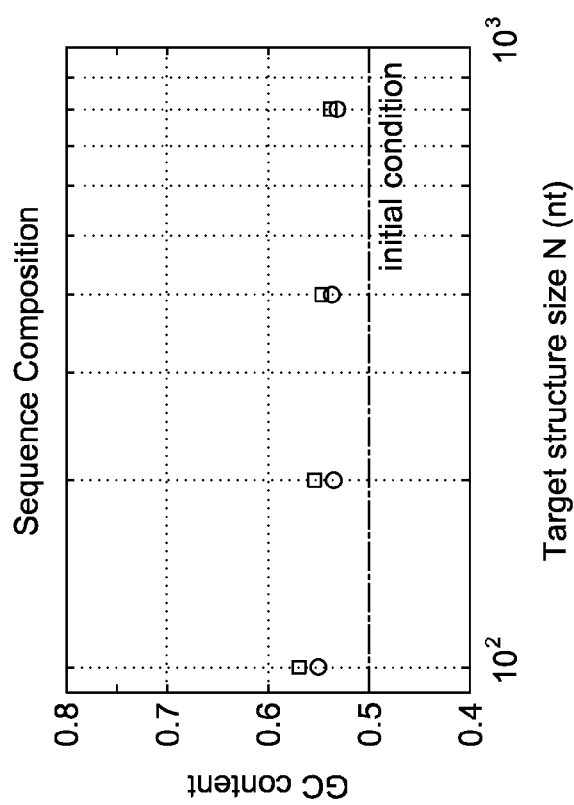
FIG. 11C
FIG. 11D

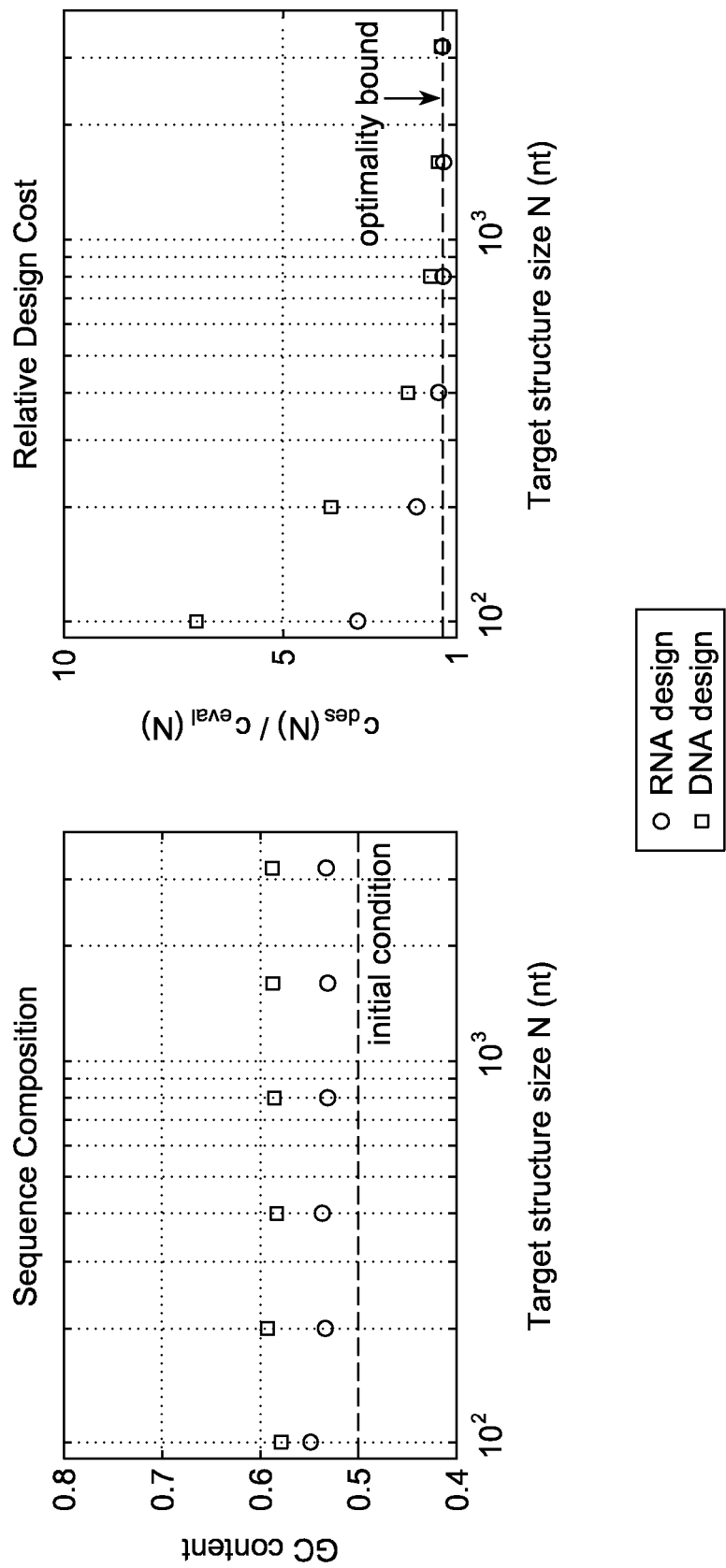

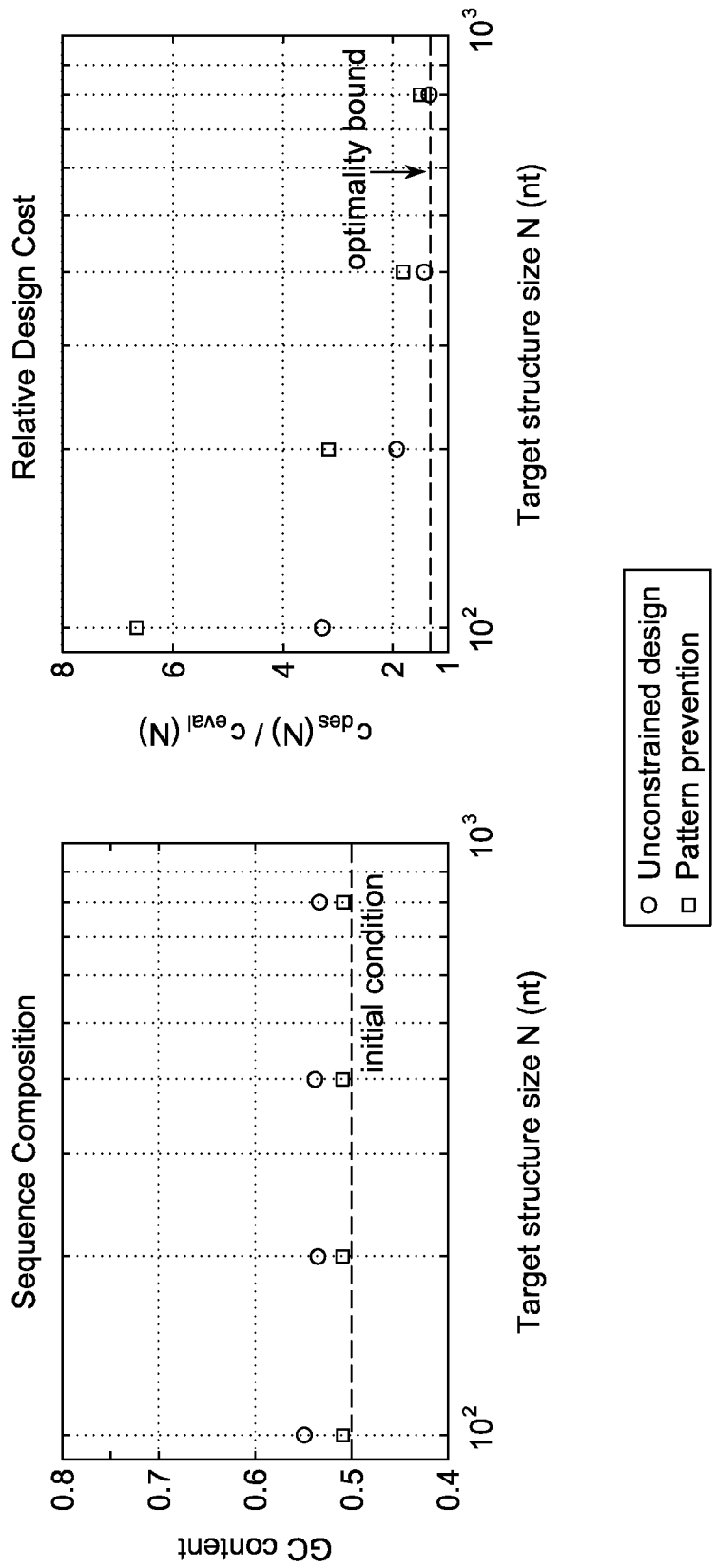

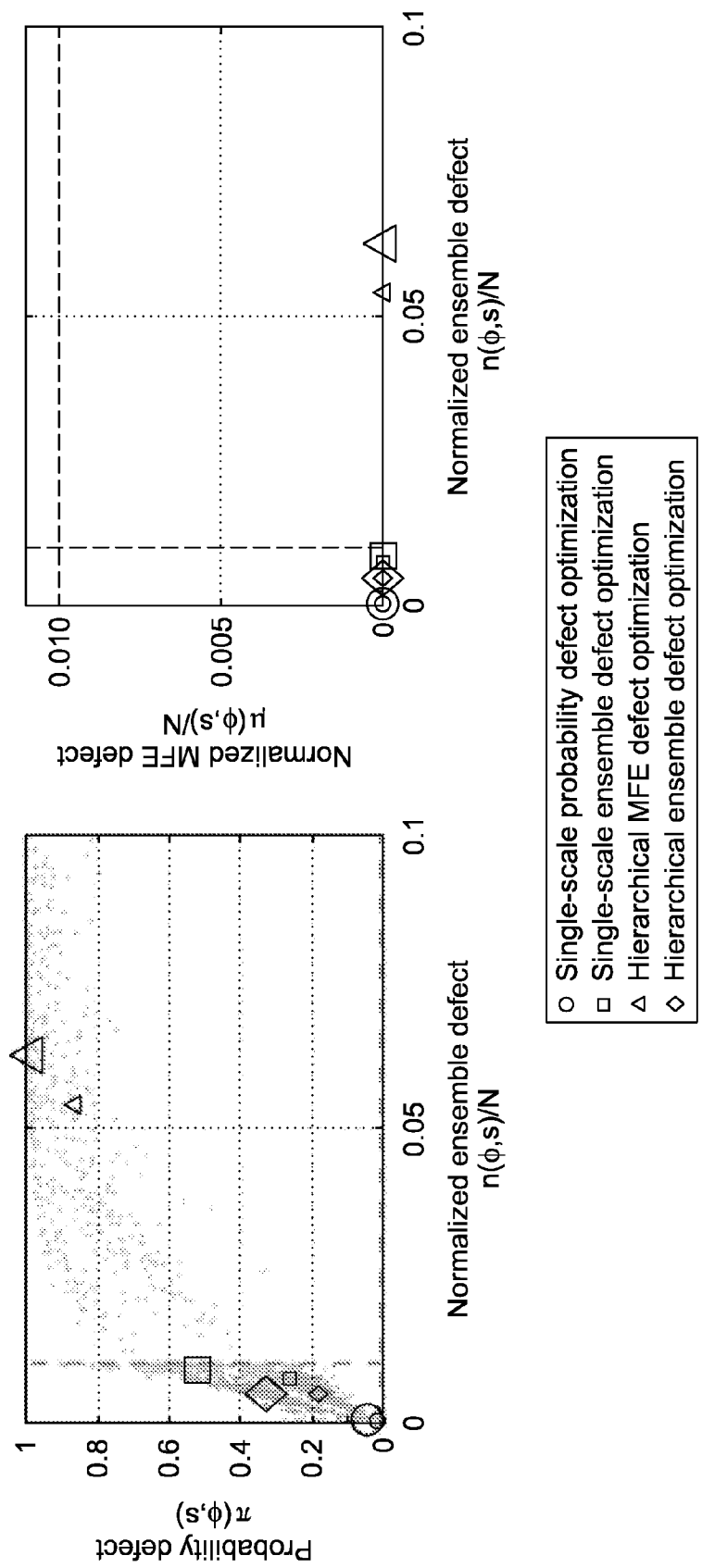

SEQUENCE LISTING

<160> NUMBER OF SEQ ID NOS: 2

<210> SEQ ID NO 1
<211> LENGTH: 18
<212> TYPE: RNA
<213> ORGANISM: Artificial Sequence
<220> FEATURE:
<223> OTHER INFORMATION: Computer Generated RNA Sequence

<400> SEQUENCE: 1
gccccggucc ccggucgc                                                 18

<210> SEQ ID NO 2
<211> LENGTH: 7
<212> TYPE: RNA
<213> ORGANISM: Artificial Sequence
<220> FEATURE:
<223> OTHER INFORMATION: Computer Generated RNA Sequence

<400> SEQUENCE: 2 gcgaggc                                                              7

SYSTEM AND METHOD FOR NUCLEIC ACID SEQUENCE DESIGN

CROSS-REFERENCE TO RELATED APPLICATIONS

This application claims priority to U.S. Provisional Application No. 61/320,863 filed on Apr. 5, 2010 and hereby incorporates by reference all of the contents described therein.

GOVERNMENTAL RIGHTS

This work was supported federal by funding from the National Science Foundation under grant numbers NSF-CCF-0832824 (The Molecular Programming Project) and NSF-CCF-CAREER-0448835. The government has rights in this invention.

BACKGROUND OF THE INVENTION

Reference to Sequence Listing

The present application includes a Sequence Listing in Electronic format. The Sequence Listing is provided as a file entitled CALTE.068A_Sequence.txt, created Jan. 23, 2013, which is approximately 1 kb in size. The information in the electronic format of the sequence listing is incorporated herein by reference in its entirety.

BACKGROUND OF THE INVENTION

The programmable chemistry of nucleic acid base pairing enables the rational design of self-assembling molecular structures, devices, and systems. However, the ability to specify a target nucleic acid structure, and then design a nucleic acid sequence that will adopt this target structure is still challenging and computationally intensive.

Secondary Structure Model

For an RNA strand with N nucleotides, the sequence, $\phi$, is specified by base identities $\phi_i \in \{A, C, G, U\}$ for $i=1, \ldots, N$ (T replaces U for DNA). The secondary structure, s, of one or more interacting RNA strands can be defined by a set of base pairs (each a Watson Crick pair [A-U or C-G] or wobble pair [G-U]). Using the set of base pairs, a polymer graph for a secondary structure can then be constructed by ordering the strands around a circle, drawing the backbones in succession from 5' to 3' around the circumference with a nick between each strand, and drawing straight lines connecting paired bases.

A secondary structure is "pseudoknotted" if every strand ordering corresponds to a polymer graph with crossing lines. A secondary structure is connected if no subset of the strands is free of the others. An "ordered complex" corresponds to the unpseudoknotted structural ensemble, $\Gamma$, comprising all connected polymer graphs with no crossing lines for a particular ordering of a set of strands. For a secondary structure, $s \in \Gamma$, the free energy, $\Delta G(\phi, s)$, is calculated using nearest-neighbor empirical parameters for RNA in 1M Na$^{+5}$ or for DNA in user-specified Na$^+$ and Mg$^{++}$ concentrations. This physical model provides the basis for rigorous analysis and design of equilibrium base-pairing in the context of the free energy landscape defined over ensemble $\Gamma$.

Characterizing Equilibrium Secondary Structure

Using this secondary energy model, the equilibrium of a nucleic acid complex can be characterized. The equilibrium state of nucleic acid complex can be determined by calculating the partition function $$Q(\phi) = \sum_{s \in \Gamma} e^{-\Delta G(\phi, s)/k_B T}$$

over the unpseudoknotted structure ensemble $\Gamma$. Using the partition function, it is possible to then evaluate the equilibrium probability $$p(\phi, s) = \frac{1}{Q(\phi)} e^{-\Delta G(\phi, s)/k_B T},$$

of any secondary structure $s \in \Gamma$. Here, $k_B$ is the Boltzmann constant and T is temperature. The secondary structure with the highest probability at equilibrium is the minimum free energy (MFE) structure, satisfying $$s^{MFE}(\phi) = \underset{s \in \Gamma}{\operatorname{argmin}} \Delta G(\phi, s).$$

The equilibrium structural features of ensemble $\Gamma$ are quantified by the base-pairing probability matrix, $P(\phi)$, with entries $P_{i,j}(\phi) \in [0, 1]$ corresponding to the probability, $$P_{i,j}(\phi) = \sum_{s \in \Gamma} p(\phi, s) S_{i,j}(s),$$

that base pair i·j forms at equilibrium. Here, S(s) defines a structure matrix with entries $S_{i,j}(s) \in \{0, 1\}$. If structure s contains pair i·j, then $S_{i,j}(s)=1$, otherwise $S_{i,j}(s)=0$. For convenience, the structure and probability matrices are augmented with an extra column to describe unpaired bases. The entry $S_{i,N+1}(s)$ is unity if base i is unpaired in structure s and zero otherwise; the entry $P_{i,N+1}(\phi) \in [0, 1]$ denotes the equilibrium probability that base i is unpaired over ensemble $\Gamma$. Hence the row sums of the augmented S(s) and $P(\phi)$ matrices are unity.

The distance between two secondary structures, $s_1$ and $s_2$, is the number of nucleotides paired differently in the two structures:

$$d(s_1, s_2) = N - \sum_{\substack{1 \le i \le N \\ 1 \le j \le N+1}} S_{i,j}(s_1) S_{i,j}(s_2).$$

The discrete delta function is defined as $$\delta_{s_1, s_2} = \begin{cases} 1, & \text{if } d(s_1, s_2) = 0 \\ 0, & \text{otherwise} \end{cases}$$

with respect to secondary structure.

Although the size of the ensemble, $\Gamma$, grows exponentially with the number of nucleotides N, the MFE structure having the lowest energy, the partition function, and the equilibrium base-pairing probabilities can be evaluated using $\Theta(N^3)$ dynamic programs.

For a given target structure, s, the determination of the nucleotide sequence that will produce the target structure s can be specified as an optimization problem, minimizing an objective function with respect to sequence, $\phi$. Rather than seeking a global optimum, optimization can be terminated if the objective function is reduced below a prescribed stop condition.

One strategy to determine the lowest free energy sequence that corresponds to a particular target structure s is to minimize the MFE defect $$\mu(\phi, s) = d(s^{MFE}, s)$$
$$= N - \sum_{\substack{1 \le i \le N \\ 1 \le j \le N+1}} S_{i,j}(s^{MFE}(\phi))S_{i,j}(s),$$

corresponding to the distance between the MFE structure $s^{MFE}(\phi)$ and the target structure s. This approach hinges on whether or not the equilibrium structural features of ensemble $\Gamma$ are well-characterized by the single structure $s^{MFE}(\phi)$, which in turn depends on the specific sequence $\phi$. If $\mu(\phi, s)=0$, the target structure s is the most probable secondary structure at equilibrium. However, $p(\phi, s)$ can nonetheless be arbitrarily small due to competition from other secondary structures in $\Gamma$.

To address this concern, an alternative strategy to MFE defect minimization is to minimize the probability defect:

$$\pi(\phi,s)=1-p(\phi,s),$$

corresponding to the sum of the probabilities of all non-target structures in the ensemble $\Gamma$. If $\pi(\phi, s) \approx 0$, the sequence design is essentially ideal because the equilibrium structural properties of the ensemble are dominated by the target structure s. However, as $\pi(\phi, s)$ deviates from zero, it increasingly fails to characterize the quality of the sequence because the probability defect treats all non-target structures as being equally defective. This property is a concern for challenging designs where it may be infeasible to achieve $\pi(\phi, s) \approx 0$.

To address these shortcomings, still another strategy is to minimize the ensemble defect between the target structure s and the equilibrium properties of sequence $\phi$. The ensemble defect $$n(\phi, s) = \sum_{\sigma \in \Gamma} p(\phi, \sigma)d(\sigma, s)$$
$$= N - \sum_{\substack{1 \le i \le N \\ 1 \le j \le N+1}} P_{i,j}(\phi)S_{i,j}(s),$$

corresponds to the average number of incorrectly paired nucleotides at equilibrium calculated over ensemble $\Gamma$.

These three objective functions, ensemble defect minimization, MFE defect minimization and probability defect minimization, and can be cast into a unified form to highlight their differences:

$$n(\phi, s) = \sum_{\sigma \in \Gamma} p(\phi, \sigma)d(\sigma, s),$$
$$\mu(\phi, s) = \sum_{\sigma \in \Gamma} \delta_{\sigma, s^{MFE}} d(\sigma, s),$$
$$\pi(\phi, s) = \sum_{\sigma \in \Gamma} p(\phi, \sigma)(1 - \delta_{\sigma,s}).$$

Using $n(\phi, s)$ to perform ensemble defect optimization, the average number of incorrectly paired nucleotides at equilibrium is evaluated over ensemble $\Gamma$ using $p(\phi, \sigma)$, the Boltzmann-weighted probability of each secondary structure $\sigma \in \Gamma$, and $d(\sigma, s)$, the distance between each secondary structure $\sigma \in \Gamma$ and the target structure s. By comparison, using $\mu(\phi, s)$ to perform MFE defect optimization, $p(\phi, \sigma)$ is replaced by the discrete delta function $\delta_{\sigma, s^{MFE}}$, which is unity for $S^{MFE}$ and zero for all other structures $\sigma \in \Gamma$. Alternatively, using $\sigma(\phi, s)$ to perform probability defect optimization, $d(\sigma, s)$ is replaced by the binary distance function $(1-\delta_{\sigma, s})$, which is zero for s and 1 for all other structures $\sigma \in \Gamma$.

Hence, the MFE defect makes the optimistic assumption that $s^{MFE}$ will dominate $\Gamma$ at equilibrium, while the probability defect makes the pessimistic assumption that all structures $\sigma \in \Gamma$ with $d(\sigma, s) \ne 0$ are equally distant from the target structure s. The objective function $n(\phi, s)$ quantifies the equilibrium structural defects of sequence $\phi$ even when $\mu(\phi, s)$ and $\pi(\phi, s)$ do not.

SUMMARY OF THE INVENTION

Described herein are systems and processes for designing the sequence of one or more interacting nucleic acid strands intended to adopt a target secondary structure at equilibrium. Sequence design is formulated as an optimization problem with the goal of reducing an ensemble defect below a user-specified stop condition. For a candidate sequence and a given target secondary structure, the ensemble defect is the average number of incorrectly paired nucleotides at equilibrium evaluated over the ensemble of unpseudoknotted secondary structures. To reduce the computational cost of accepting or rejecting mutations to a random initial sequence, candidate mutations are evaluated on leaf nodes of a tree-decomposition of the target structure.

As described in more detail below, during leaf optimization, defect-weighted mutation sampling is used to select each candidate mutation position with probability proportional to its contribution to the ensemble defect of the leaf. As subsequences are merged moving up the tree, emergent structural defects resulting from crosstalk between sibling sequences are eliminated via reoptimization within the defective subtree starting from new random subsequences. Using a $\Theta(N^3)$ dynamic program to evaluate the ensemble defect of a target structure with N nucleotides, this hierarchical approach implies an asymptotic optimality bound on design time. Thus, for sufficiently large N, the cost of sequence design is bounded below by 4/3 the cost of a single evaluation of the ensemble defect for the full sequence. Hence, the design process has time complexity $\Omega(N^3)$. For target structures containing $N \in \{100, 200, 400, 800, 1600, 3200\}$ nucleotides and duplex stems ranging from 1 to 30 base pairs, RNA sequence designs at 37° C. typically succeed in satisfying a stop condition with ensemble defect less than N/100. Empirically, the sequence design process exhibits asymptotic optimality and the exponent in the time complexity bound is sharp. This demonstrates a great improvement over prior systems that did not demonstrate this asymptotic optimality.

An embodiment is an electronic system for optimizing the sequence of a nucleic acid strand to adopt a specific target secondary structure at equilibrium. This embodiment of the system includes: an input for receiving a target secondary structure; a hierarchical structure decomposition module configured to decompose the target secondary structure at split points into a tree of parental nodes, child nodes and leaf nodes wherein each split point is formed within a duplex stem of the target structure; a leaf optimization module configured to determine a leaf nucleotide sequence of the target structure at each leaf node in the tree; and a merging module configured to recurse the nodes of the tree and merge the determined leaf nucleotide sequences at each node to optimize the nucleotide sequence of a nucleic acid strand that adopts the specific target secondary structure at equilibrium.

Yet another embodiment is a method in an electronic system for designing a nucleotide sequence to adopt a target secondary structure at equilibrium. This method includes: decomposing a target secondary structure of a nucleic acid molecule into a tree structure having leaves and nodes, wherein the decomposition takes place at splice points within duplex stems of the target secondary structure; designing a nucleotide sequence for each leaf within the binary tree; recursing the tree to merge and reoptimize the nucleotide sequence for each node of the tree; and determining the nucleotide sequence of the root node from the merged and reoptimized nucleotide sequences of the other nodes in the tree.

One other embodiment is an electronic system for designing a nucleotide sequence to adopt a target secondary structure at equilibrium. In this embodiment, the system includes means for decomposing a target secondary structure of a nucleic acid molecule into a tree having leaves and nodes, wherein the decomposition takes place at splice points within duplex stems of the target secondary structure; means for designing a nucleotide sequence for each leaf within the binary tree; means for recursing the tree to merge and reoptimize the nucleotide sequence for each node of the tree; and means for determining the nucleotide sequence of the root node from the merged and reoptimized nucleotide sequences of the other nodes in the tree.

Still another embodiment is a programmed storage device having instructions that when executed perform a method that includes: decomposing a target secondary structure of a nucleic acid molecule into a tree having leaves and nodes, wherein the decomposition takes place at splice points within duplex stems of the target secondary structure; designing a nucleotide sequence for each leaf within the binary tree; recursing the tree to merge and reoptimize the nucleotide sequence for each node of the tree; and determining the nucleotide sequence of the root node from the merged and reoptimized nucleotide sequences of the other nodes in the tree.

BRIEF DESCRIPTION OF THE DRAWINGS

FIG. 4 shows pseudocode descriptions of the functions "DesignSeq", "UpdateChildren" and "OptimizeLeaf" found in certain of the disclosed embodiments.

FIG. 5a is a histogram showing the fraction of bases paired in each structure for both test sets. FIG. 5b is a histogram counting the number of structures with a given number of stems. FIG. 5c is a histogram which shows the number of stems of each length in each test set.

FIGS. 6a-6d are plots showing the performance of certain embodiments of the system as the target structure size is increased. Particularly, FIG. 6a depicts the median relative ensemble defect after applying the design process to the engineered and random test set of target structures. FIG. 6b depicts the median time cost of applying the design process to the engineered and a random test set of target structures. FIG. 6c depicts the relative guanine-cytosine content after applying the design process to the engineered and a random test set of target structures. FIG. 6d depicts the design time cost, relative to the objective function evaluation cost, of applying certain processes to the engineered and a random test set of target structures.

FIGS. 7a and 7b depict the degree leaf independence in the design process for the engineered and random test set, respectively. They show ensemble defects of the leaves vs the root ensemble defects for initial sequences, sequences in which the leaves are designed and sequences after merging and reoptimization.

FIGS. 8a-8d are plots highlighting the effects of hierarchical structure decomposition and defect-weighted sampling on performance of certain embodiments on the engineered test set. Particularly, FIG. 8a depicts the relative ensemble defect after applying embodiments with and without hierarchical decomposition and with and without defect-weighted mutation sampling to each of a uniform sampling and defect-weighted sampling dataset for each of single-scale optimization and hierarchical optimization methods. FIG. 8b depicts the time cost of applying single-scale embodiments, hierarchically decomposing embodiments, uniform mutation sampling embodiments and defect-weighted mutation sampling embodiments. FIG. 8c depicts the relative guanine-cytosine content after applying the above embodiments. FIG. 8d depicts the design cost, relative to the objective function evaluation cost, of the embodiments.

FIG. 9a depicts the relative median ensemble defect resulting from each initial sequence type. FIG. 9b depicts the time cost resulting from each initial sequence type. FIG. 9c depicts the relative guanine-cytosine content resulting from each initial sequence type. FIG. 9d depicts the design cost relative to the objective function evaluation cost, resulting from each initial sequence type.

FIGS. 10a-10d show plots of the effects of a selected stop condition stringency on performance for certain embodiments of the invention. Particularly, five degrees of stop condition stringency are considered: $f_{stop}=0.001$, $f_{stop}=0.005$, $f_{stop}=0.01$ $f_{stop}=0.05$, and $f_{stop}=0.1$. Each stringency was tested using the engineered test set. FIG. 10a depicts the median normalized ensemble defect resulting from each of the stop condition stringencies. FIG. 10b depicts the time cost of each of the stop condition stringencies. FIG. 10c depicts the relative guanine-cytosine content of each of the stop condition stringencies. FIG. 10d depicts the design cost, relative to the objective function cost, resulting from each of the stop condition stringencies.

FIGS. 11a-11d show plots of the effects of single and multi-stranded structures on performance for certain embodiments of the invention. Structures were selected from the engineered test set. FIG. 11a depicts the median ensemble defect for each length of single and multi-stranded structures. FIG. 11b depicts the relative time cost resulting from each of single and multi-stranded structures. FIG. 11c depicts the relative guanine-cytosine content resulting from each of single and multi-stranded structures. FIG. 11d depicts the median design cost, relative to the objective function cost, resulting from each length of single and multi-stranded structures.

FIGS. 12a-12d show plots of the effects of the selected design material on performance for certain embodiments of the invention. Structures were selected from the engineered test set. FIG. 12a depicts the median normalized ensemble defect resulting from each structure length. FIG. 12b depicts the normalized median time cost resulting from each structure length. FIG. 12c depicts the guanine-cytosine content resulting from each structure length. FIG. 12d depicts the design cost, relative to the objective function cost.

FIGS. 13a-13d show plots of the effects of pattern prevention for certain of the embodiments described herein. Structures were selected from the engineered test set. FIG. 13a depicts the median normalized ensemble defect resulting from each of unconstrained designs and designs with pattern preventions. FIG. 13b depicts the relative time cost resulting from each of unconstrained designs and designs with pattern preventions. FIG. 13c depicts the relative guanine-cytosine content resulting from each of unconstrained designs and designs with pattern preventions. FIG. 13d depicts the relative design cost, as measured by the objective function, resulting from each of unconstrained designs and designs with pattern preventions.

FIGS. 15a-15f are plots of the effects of different objective functions and variations on the embodiments described herein, specifically embodiments using single-scale methods to optimize the probability defect, single-scale methods to optimize the ensemble defect, hierarchical methods to optimize the MFE defect, and hierarchical methods to optimize the ensemble defect. These embodiments are all tested on the engineered test set. Particularly, FIG. 15a depicts the median normalized ensemble defect after applying these embodiments. FIG. 15b depicts the relative time cost after applying these embodiments. FIG. 15c depicts the relative guanine-cytosine content after applying these embodiments. FIG. 15d depicts the relative design cost of applying these embodiments. FIGS. 15e and 15f depict design quality of the four embodiments, showing the probability defect relative to the normalized ensemble defect and the normalized MFE defect relative to the normalized ensemble defect.

DETAILED DESCRIPTION

Figure 1:
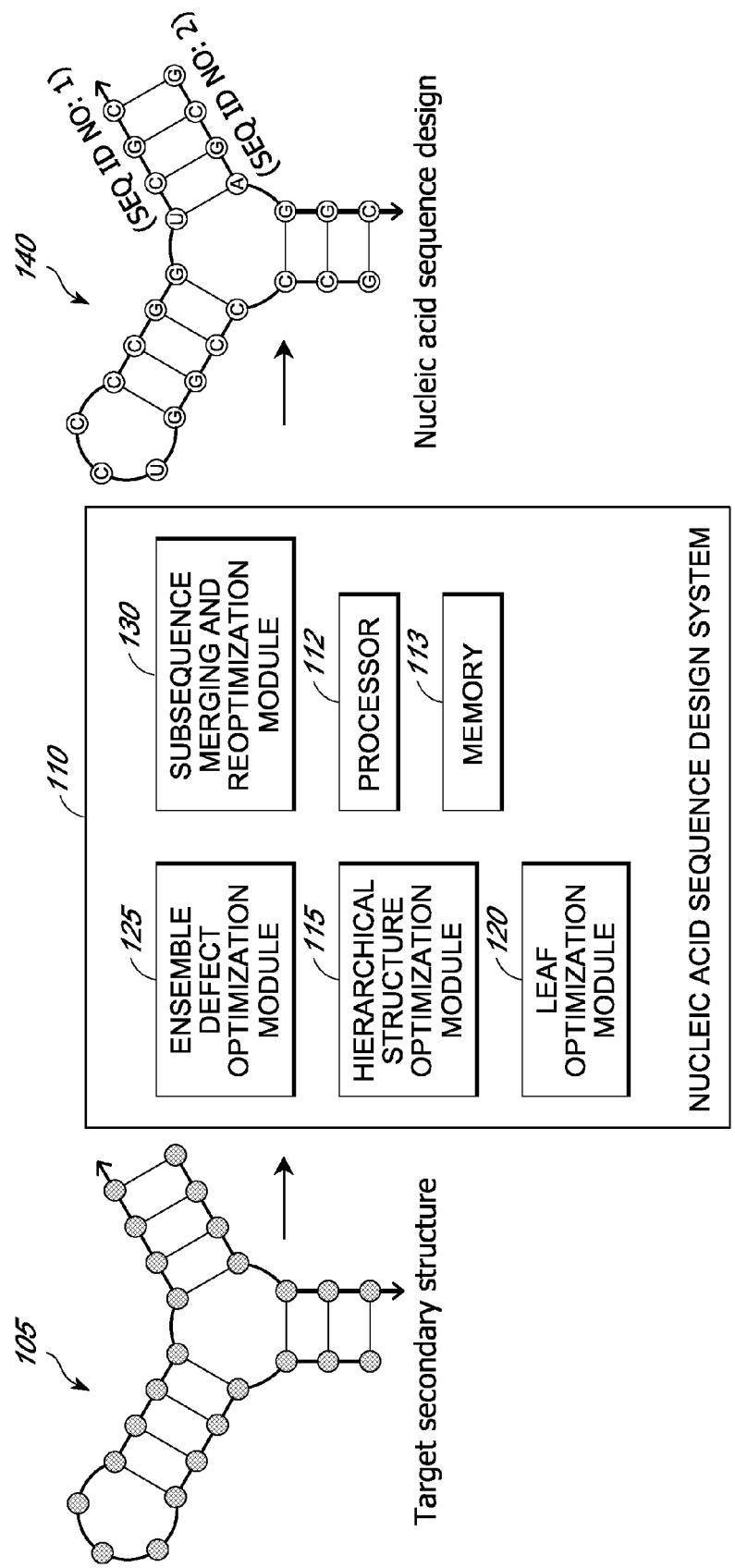
FIG. 1 is a block diagram depicting certain embodiments of a nucleic acid sequence design system, wherein a sequence is designed for a proposed secondary structure.

Embodiments of the invention relate to systems and processes for designing nucleic acid molecules that meet a target design criteria. In one embodiment, a single target unpseudoknotted structure having predetermined design criteria is input into the system. The target structure may include one or more nucleic acid molecule chains of unknown sequence. As described in more detail below, the system uses the target unpseudoknotted structure to optimize the base composition of one or more nucleotide sequences that will base pair together into a secondary structure that meets the target design criteria. This system is useful in order to design nucleic acid molecules that assemble in vitro or in vivo into target structures.

In one embodiment, the system is used to design small conditional RNAs that are used in a hybridization chain reaction (HCR). The HCR is described in U.S. Pat. No. 7,727,721 issued on Jun. 1, 2010, which is incorporated herein by reference in its entirety. These small conditional RNAs form target secondary structures that change conformation upon detection of a particular signal (Dirks R M, Pierce N A (2004) Triggered amplification by hybridization chain reaction. *Proc Natl Acad Sci USA* 101:15275-15278). For example, small conditional RNAs have been designed to self-assemble and disassemble along a predetermined pathway in order to perform dynamic functions (Yin, et al, (2008) Programming biomolecular self-assembly pathways *Nature* 451:318-322). Small conditional RNAs can cause selective cell death of cancer cells (Venkataramanm, et al, (2010) Selective cell death mediated by small conditional RNAs, *Proc Natl Acad Sci USA* 107:16777-16782) and have been used in multiplexed fluorescent in situ hybridization assays to map mRNA expression within intact biological samples (Choi, et al. (2010) Programmable in situ amplification for multiplexed imaging of mRNA expression *Nature. Biotechnol.* 28:1208-1212). The disclosed embodiments provide a nucleic acid molecule design process and system that achieves high design quality while maintaining a low computational overhead.

In one example, the system may use separate sub-processes to design a polynucleotide sequence $\phi$ of one or more strands that will form into a target secondary structure s at equilibrium. The system optimizes the ensemble defect of this target structure using several primary processes. The three main sub-processes in this embodiment are hierarchical structure decomposition of the target structure, leaf optimization with defect-weighted mutation sampling, and subsequence merging and reoptimization, each of which is described in more detail below. Equilibrium can be at 1M $Na^+$, or designated by user-specified $Na^+$ and $Mg^{++}$ concentrations.

In one embodiment a target nucleotide sequence secondary structure is defined as a structure matrix $S(s)$ with entries $S_{i,j}(s) \in \{0, 1\}$. If structure s contains pair i·j, then $S_{i,j}(s)=1$, otherwise $S_{i,j}(s)=0$. The system performs hierarchical structure decomposition on the target secondary structure s, defect-weighted sampling on the leaves, and merging and reoptimization as it traverses up the decomposition tree. The hierarchical structure decomposition identifies stem structures within the target structure s, and divides the root structure into a tree of substructures. In one embodiment, the tree of substructures is a binary tree of substructures. The minimum number of nucleotides in a node can be set by the user. If a node can be divided into two nodes, both of which contain more than the minimum number of nucleotides, then the node is divided. For a given target secondary structure, s, with N nucleotides, we seek to design a sequence, $\phi$, with ensemble defect, $n(\phi, s)$, satisfying the stop condition:

$$n(\phi, s) \le f_{stop} N,$$

for a user-specified value of $f_{stop} \in (0, 1)$. Using ensemble defect analysis, candidate mutations in a test nucleotide sequence are evaluated at the leaves of the binary tree decomposition of the target structure. During leaf optimization, defect-weighted mutation sampling is used to select each candidate mutation position with probability proportional to its contribution to the ensemble defect of the leaf. Mutations are accepted if they decrease the leaf ensemble defect. Subsequences are merged moving up the tree and parental ensemble defects are evaluated. If emergent structural defects are encountered when merging subsequences, they are eliminated via defect-weighted child sampling and reoptimization. After all of the subsequences have been merged, the final result is a nucleotide sequence $\phi$ that has a minimized ensemble defect when folded into the target structure s. Because the minimization of the ensemble defect is performed by recursing nodes and leaves of the binary tree, the process is computationally much more efficient than prior systems that optimized the objective function over entire nucleotide sequence $\phi$.

DEFINITIONS

As used herein, an "input device" can be, for example, a keyboard, rollerball, mouse, voice recognition system or other device capable of transmitting information from a user to a computer. The input device can also be a touch screen associated with the display, in which case the user responds to prompts on the display by touching the screen. The user may enter textual information through the input device such as the keyboard or the touch-screen.

The invention is operational with numerous other general purpose or special purpose computing system environments or configurations. Examples of well-known computing systems, environments, and/or configurations that may be suitable fore use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices.

As used herein, "instructions" refer to computer-implemented steps for processing information in the system. Instructions can be implemented in software, firmware or hardware and include any type of programmed step undertaken by components of the system.

A "microprocessor" or "processor" may be any conventional general purpose single- or multi-core microprocessor such as a Pentium® processor, Intel® Core™, a 8051 processor, a MIPS® processor, or an ALPHA® processor. In addition, the microprocessor may be any conventional special purpose microprocessor such as a digital signal processor or a graphics processor.

The system is comprised of various modules as discussed in detail below. As can be appreciated by one of ordinary skill in the art, each of the modules comprises various sub-routines, procedures, definitional statements and macros. Each of the modules are typically separately compiled and linked into a single executable program. Therefore, the following description of each of the modules is used for convenience to describe the functionality of the preferred system. Thus, the processes that are undergone by each of the modules may be arbitrarily redistributed to one of the other modules, combined together in a single module, or made available in, for example, a shareable dynamic link library.

The system may be used in connection with various operating systems such as SNOW LEOPARD®, iOS®, LINUX, UNIX or MICROSOFT WINDOWS®.

The system may be written in any conventional programming language such as C, C++, BASIC, Pascal, or Java, and run under a conventional operating system.

A web browser comprising a web browser user interface may be used to display information (such as textual and graphical information) to a user. The web browser may comprise any type of visual display capable of displaying information received via a network. Examples of web browsers include Microsoft's Internet Explorer browser, Mozilla's Firefox browser, Apple Safari and PalmSource's Web Browser, or any other browsing or other application software capable of communicating with a network.

The invention disclosed herein may be implemented as a method, apparatus or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

In addition, the modules or instructions may be stored onto one or more programmable storage devices, such as FLASH drives, CD-ROMs, hard disks, and DVDs. One embodiment includes a programmable storage device having instructions stored thereon that when executed perform the methods described herein to determine nucleic acid sequence information.

As used herein, a "node" is a structure which may contain a value, a condition, or represent a separate data structure (which could be a tree of its own). Each node in a tree has zero or more child nodes, which are below it in the tree (by convention, trees are drawn growing downwards). A node that has a child is called the child's parent node (or ancestor node, or superior). A node typically has at most one parent. As is known, nodes that do not have any children are called leaf nodes or terminal nodes.

The topmost node in a tree is the root node. An internal node or inner node is any node of a tree that has child nodes and is thus is not considered to be a leaf node. Similarly, an external node or outer node is any node that does not have child nodes and is thus a leaf node A subtree of a tree is a tree consisting of a node in the tree and all of its descendants in the tree. For example, the subtree corresponding to the root node is the entire tree. The subtree that corresponds to any other node may be called a proper subtree.

System Overview

FIG. 1 shows one embodiment of a system 100 for determining the nucleic acid sequence, or sequences that will form a target structure. The system includes a processor 102 configured to run instructions provided by each module within the system 100. As shown, a target secondary structure 105 is input into a nucleic acid sequence design system 110. The sequence design system 110 includes a memory 113 and a display output 114. The memory 113 can be any type of conventional RAM or ROM memory, configured to store, receive, and buffer instructions, data or other information used within the system 110. The display output 114 is configured to link with a conventional monitor or other device for showing textual or graphical information output by the system 110. In one embodiment, the system 110 is an Internet server and the target structure is provided from an Internet user accessing the server.

Also within the nucleic acid design system 110 is a hierarchical structure decomposition module 115 that contains instructions for dividing the larger target structure into a memory structure comprising a binary tree that has nodes and leaves for further analysis. Thus, the hierarchical structure decomposition module 115 provides one means for decomposing a target nucleic acid structure. Each node or leaf may correspond to a stem, or stem fragment of the target structure s. In order minimize emergent errors that may occur when the target structures in the leaf nodes are later rejoined, one or more "dummy" or spacer nucleotides can be added to the ends of the structures within each leaf so that the leaf structure more accurately mimics the performance of the larger overall target structure. The memory structure of the binary tree may be stored within the memory 113 of the system 110.

Figure 2:
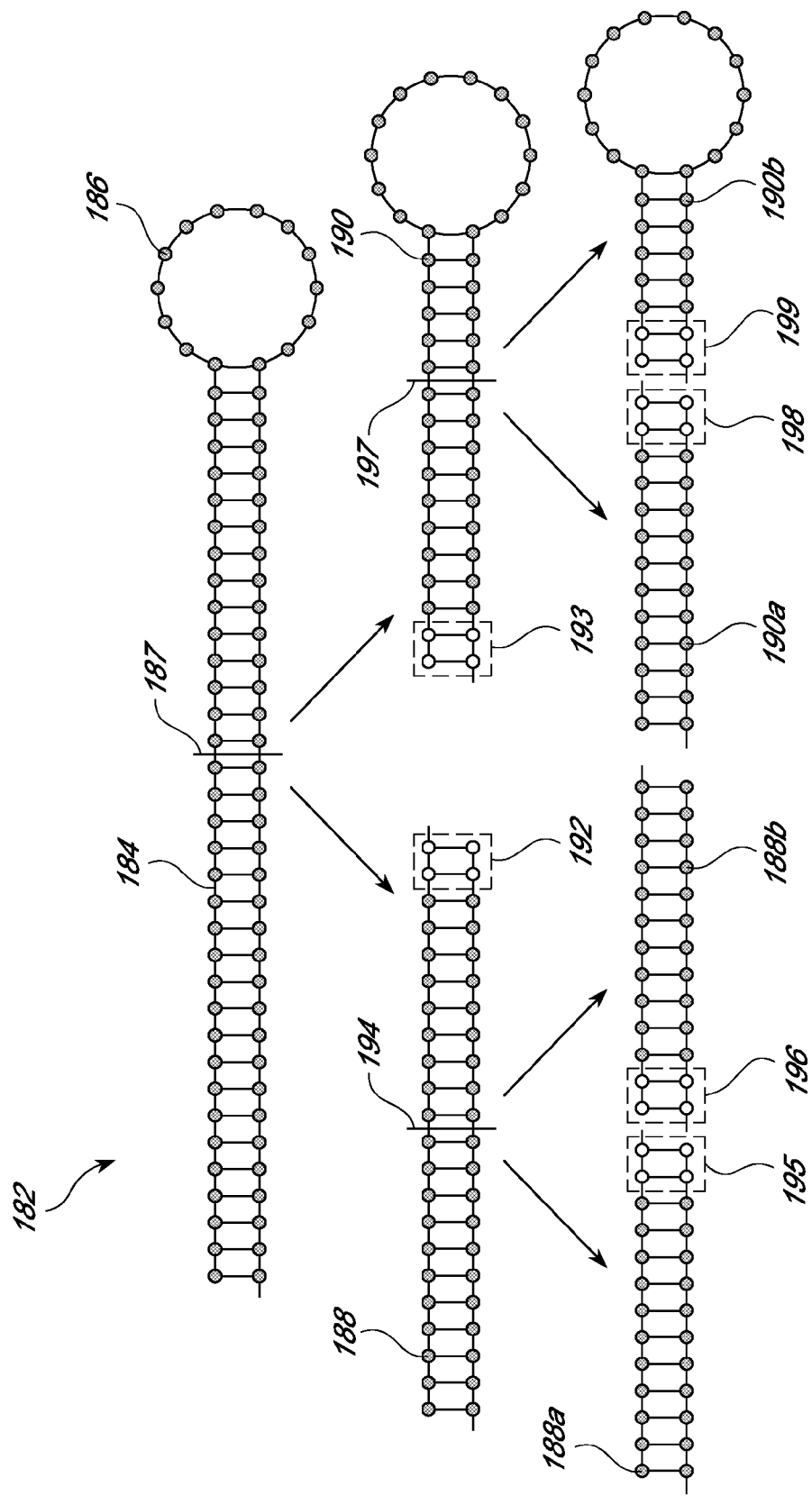
FIG. 2 is a schematic illustration of one embodiment of a method for performing a hierarchical decomposition of a target structure.

One schematic representation of a method of decomposing a target structure 182 is shown in FIG. 2. As shown, the target structure 182 includes a stem 184 and loop 186. In a first step in the decomposition, the stem 184 is divided approximately in half at a split point 187 to create a first stem portion 188 and a second stem and loop portion 190. A set of two base-paired dummy nucleotides 192 are added to the first stem portion 188. A set of two base-paired dummy nucleotides 193 are then added to the second stem and loop portion 190. Thus, in this embodiment, the system adds dummy nucleotides to either side of the split point 187. In a second step in the decomposition, the first stem portion 188 is divided approximately in half at a split point 194 to result in the formation of leaf fragments 188a and 188b. Dummy nucleotide sets 195 and 196 are added to either side of the split point 194. Similarly, at the second step, the stem and loop portion 190 is divided approximately in half at a split point 197 to yield leaf fragments 190a and 190b. Dummy nucleotides sets 198 and 199 are added to either side of the split point 197. This schematic representation thus illustrates one embodiment of a method for decomposing a target structure at its stem portions into a tree comprising nodes and leaves.

Referring back to FIG. 1, the system 110 also includes a leaf optimization module 120 that receives data representing the leaves and nodes of the decomposed binary tree. The leaf optimization module 120 has instructions for selecting a first random nucleotide sequence to be compared against the decomposed target structure at the selected leaf. Thus, the leaf optimization module provides one means for optimizing nucleic acid sequences in leaf nodes of a hierarchical tree. An ensemble defect optimization module 125 is provided within the system 110, and contains instructions to use ensemble defect optimization to determine the ensemble distance of the random nucleotide sequence from the target structure.

If the random nucleotide sequence has a normalized ensemble defect greater than the stop condition, then the leaf optimization module 120 also provides instructions for mutating the random nucleotide sequence, and recalculating the ensemble defect of the mutated sequence. Once the leaf optimization module 120 has performed enough rounds of optimization so that the ensemble defect is below the leaf stop condition, a subsequence merging and reoptimization module 130 is used to merge two or more optimized leaves into a node. In one embodiment, the dummy nucleotides are first removed from each leaf target structure prior to merger with an upper node. Thus, the subsequence merging and reoptimization module 130 provides one means for recursing the tree to merge and reoptimize the nucleotide sequence for each node of the tree.

The pair probabilities of the merged nucleotide sequence are then compared against the target structure at that node to determine whether the merged sequences meet a predetermined stop condition or minimum free energy. If the stop condition is reached, then the subsequence merging and reoptimization module recurses down a layer in the binary tree to re-optimize the child sequences prior to merger. If the stop condition is not reached, then the subsequence merger and reoptimization module 130 continues recursing up the binary tree until the entire nucleotide sequence corresponding to a target structure 140 has been determined. Thus, the subsequence merging and reoptimization module also provides one means for determining the nucleotide sequence of the root node of the tree from the merged and reoptimized nucleotide sequences of the other nodes in the tree. Additional details on the modules within the system 110 are described in more detail with regard to FIG. 3.

Process Flow

Figure 3:
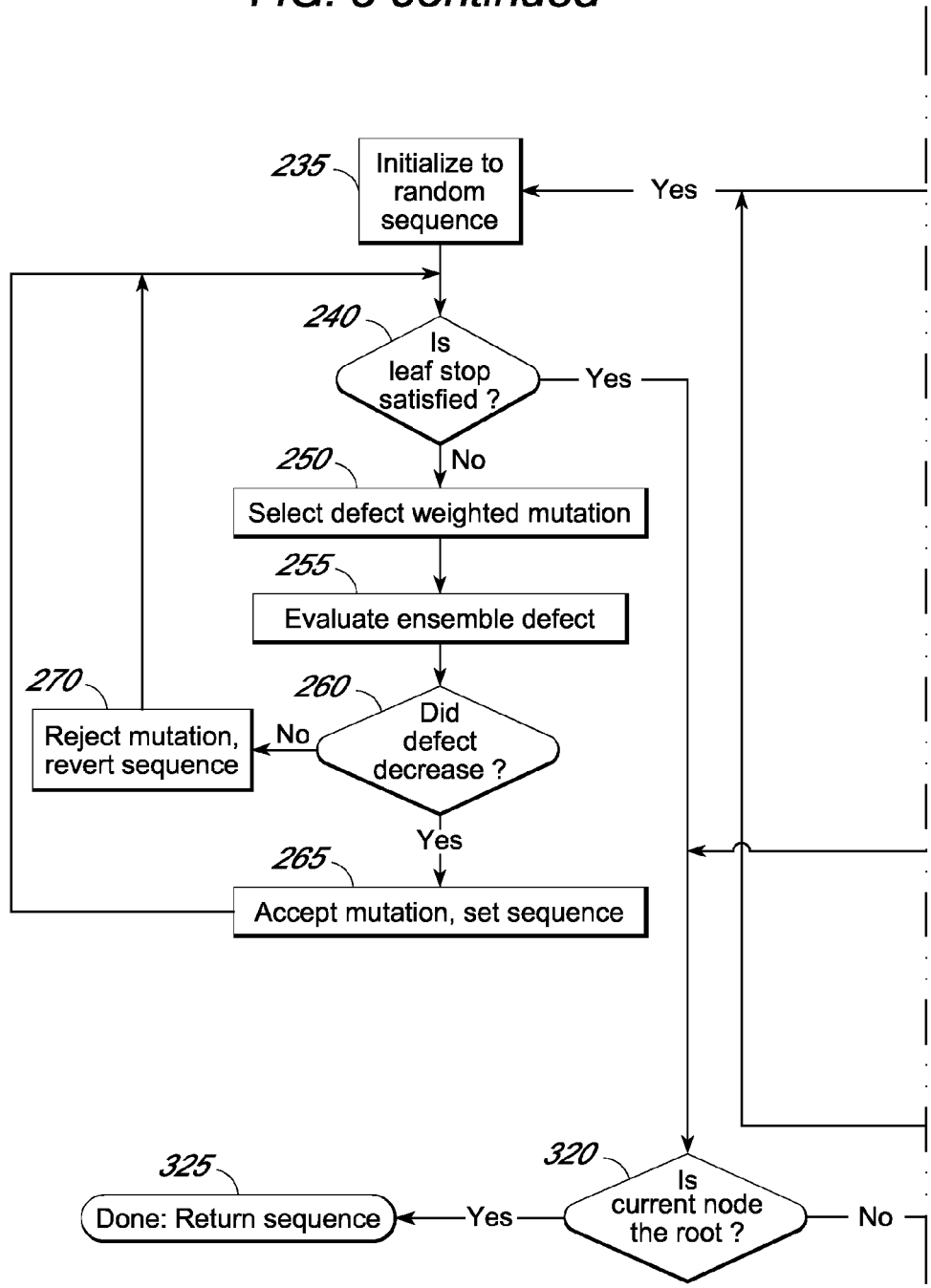
FIG. 3 is a flow diagram showing one embodiment of a process for determining a nucleotide sequence having a target structure at equilibrium.

Referring now to FIG. 3, a process 200 for determining a minimum free energy nucleotide sequence that corresponds to a target structure s is shown. The process 200 starts at a start state 205 and moves to a state 210 wherein a target structure is received by the system for analysis. In one embodiment the target nucleotide sequence secondary structure is provided using dot-parens-plus notation to denote a secondary structure. In this notation, each unpaired base is represented by a dot, each base pair is denoted by matching parentheses, and each nick between strands by a plus. An additional notation, called HU+ allows a user to specify secondary structures by specifying sizes of structural elements instead of individual base pairs. In this notation, helices are represented by Hx and unpaired regions by Ux, where x represents the size of a helix or unpaired region. Each helix is followed immediately by the substructure that is "enclosed" by the helix. If this substructure includes more than one element, parentheses are used to denote scope. A nick between strands is specified by a +. The system 110 can convert this notation into a structure matrix $S(s)$ with entries $S_{i,j}(s) \in \{0, 1\}$. If structure s contains pair i·j, then $S_{i,j}(s)=1$, otherwise $S_{i,j}(s)=0$. Of course, other formats defining the target structure are also contemplated within embodiments of the invention. Alternatively, the target structure can be provided directly as a matrix $S(s)$.

Once the target structure s has been received by the system at the state 210, the process 200 moves to a state 215 wherein the hierarchical structure decomposition module 115 (FIG. 1) is executed to decompose the structure s into a binary tree. By performing a binary tree decomposition of the target secondary structure s, each parent structure within a duplex stem of the test molecule is decomposed into smaller nodes on the binary tree. The target structure s may be decomposed into a balanced, or unbalanced, binary tree of substructures, with each node of the tree indexed by a unique integer k. For each parent node, k, there is a left child node, $k_l$, and a right child node, $k_r$. Each nucleotide in parent structure $s^k$ is partitioned to either the left or right child substructure ($s^k = s_l^k \cup s_r^k$ and $s_l^k \cap s_r^k = 0$). Child node $k_l$ inherits from parent node k the augmented substructure, $s_{l+}^k$, comprising native nucleotides, $s_{native}^{k_l} \equiv s_l^k$. The process 100 can them move to state 220 where additional dummy nucleotides that approximate the influence of its sibling in the context of their parent ($s^{k_l} \equiv s_{native}^{k_l} \cup s_{dummy}^{k_l} \equiv s_{l+}^k$). Thus, after decomposing a particular stem of the target structure, dummy nucleotide pairs can be added at a state 220 to extend the truncated duplex molecules in each child structure to mimic the parental environment.

In contrast to earlier hierarchical methods that decompose parent structures at multiloops, this hierarchical tree structure decomposes parent structures within duplex stems within the target structure s. Eligible split-points within each stem are those locations within a duplex stem with at least $H_{split}$ consecutive base-pairs to either side, such that both children would have at least $N_{split}$ nucleotides. If there are no eligible split-points, a structure becomes a leaf node in the decomposition tree. Otherwise, an eligible split-point is selected so as to minimize the difference in the size of the children, $\|s_l^k\| - \|s_r^k\|$. In order to minimize emergent defects resulting from crosstalk between child subsequences in one embodiment, dummy nucleotides are introduced into the children to compensate for the fact that the stem has been divided into multiple sequences for analysis. Dummy nucleotides can be defined by extending the newly-split duplex stem across the split-point by $H_{split}$ base pairs ($|s_{dummy}^{k_l}| = 2H_{split}$).

For a parent node k, the sequence $\phi^k$ follows the same partitioning as the structure $s^k$ ($\phi^k = \phi_l^k \cup \phi_r^k$ and $\phi_l^k \cap \phi_r^k = \phi$). Likewise, for a child node $k_l$, the sequence may contain both native and dummy nucleotides ($\phi^{k_l} \equiv \phi_{native}^{k_l} \cup \phi_{dummy}^{k_l} \equiv \phi_{l+}^k$).

Once the target secondary structure has been decomposed into nodes and leaves, and dummy nucleotides added where necessary, the process 200 moves to a state 225 wherein the root node of the binary tree is selected for analysis.

Leaf Optimization with Defect-Weighted Mutation Sampling

Once the first node for analysis has been selected at the state 225, the process 200 moves to a state 230 to determine whether to perform defect-weighted mutation sampling or to further recurse in the decomposition tree. If the node is a leaf, the process 200 moves to perform defect-weighted mutation sampling (states 235, 240, 250, 255, 260, 265, 270). If the node is not a leave, the process 200 recursively optimizes the left, then the right child nodes.

If a determination was made at the decision state 230 that the current node was a leaf, then defect-weighted mutation sampling starts from a random initial sequence at a state 235. The process 200 then moves to a decision state 240 to determine if a leaf stop condition has been satisfied. If the current sequence satisfies the stop condition, optimization stops and the process 200 moves to a state 320 to decide whether the current node is the root node. However, if a determination is made at the decision state 240 that the leaf stop condition has not been satisfied, then a mutation position is chosen using defect-weighted mutation sampling in a state 250. The process 200 then evaluates the ensemble defect at a state 255. The process 200 then moves to a decision state 260 to determine whether to accept the mutation or not. If the ensemble defect is found to have decreased due to the mutation, then the process moves to a state 265 and the mutation is accepted and the process returns to state 240 to determine if a leaf stop condition has been satisfied. However, if the ensemble defect is not found to have decreased at the decision state 260, then the process moves to a state 270, the mutation is rejected, and the process returns to state 240 to determine if a leaf stop condition has been satisfied.

In order to calculate the average number of mispaired nucleotides in the test nucleotide sequence in comparison to the target structure, the state 255 may call the ensemble defect evaluation module 125 (FIG. 1). The design objective function is the ensemble defect, $n(\phi, s)$, representing the average number of incorrectly paired nucleotides of the test nucleotide sequence at equilibrium calculated over the ensemble of unpseudoknotted secondary structures $\Gamma$. For a target leaf structure with N nucleotides, we seek to satisfy the stop condition: $n(\phi, s) \leq f_{stop} N$. As described in more detail below, ensemble defect optimization is calculated by minimizing $n(\phi, s)$ with respect to sequence $\phi$.

After analyzing the initial random test nucleotide sequence, a sequence optimization process is performed by the leaf optimization module 120 for each leaf node using defect-weighted mutation sampling in which each candidate mutation position is selected with probability proportional to its contribution to the ensemble defect of the leaf.

At leaf node k, sequence optimization is performed by mutating either one base at a time (if $S_{i,|s^k|+1}^k = 1$) or one base pair at a time (if $S_{i,j}^k = 1$ for some $1 \leq j \leq |s^k|$, in which case $\phi_i^k$ and $\phi_j^k$ are mutated simultaneously so as to remain Watson-Crick complements).

Defect-weighted mutation sampling by selecting nucleotide i as a candidate for mutation with probability $n_i^k / n^k$. A candidate sequence $\hat{\phi}^k$ is evaluated via calculation of $\hat{n}^k$ if the candidate mutation, $\xi$, is not in the set of previously rejected mutations, $\gamma_{unfavorable}$ (position and sequence). A candidate mutation is retained if $\hat{n}^k < n^k$ and rejected otherwise. The set, $\gamma_{unfavorable}$, is updated after each unsuccessful mutation and cleared after each successful mutation.

Optimization of leaf k at state 240 terminates successfully if the leaf stop condition:

$$n^k \leq f_{stop} |s^k|$$

is satisfied, or restarts if $M_{unfavorable} |s^k|$ consecutive unfavorable candidate mutations are either in unfavorable or are evaluated and added to $\gamma_{unfavorable}$. Leaf optimization is attempted from new random initial conditions up to $M_{leafopt}$ times before terminating unsuccessfully. The outcome of leaf optimization is the leaf sequence $\phi^k$ corresponding to the lowest encountered value of the leaf ensemble defect $n^k$.

After a leaf optimization has been performed for a first leaf of a selected node at the state 240, the process 200 moves to the decision state 320 to determine if the current node is a root node, and thereby the process can move up the decomposition tree. If a determination was made at the decision state 320 that the current node is not a root node, then the process 200 moves to a state 315 to set the current node to the parent of the current node. The process then moves to a state 275 to determine if the nucleotide sequence at the left child node of the parent has been designed. If the nucleotide sequence has not been designed, then the process sets the current node to the left child at a state 305 and moves to decision state 230 to determine if the current node is a leaf node.

However, if the nucleotide sequence of the left child node has been designed at the decision state 275, then the process 200 moves to a decision state 280 to determine if the right child has been designed. If the right child has not been designed, then the current node is set to the right child node at a state 310 and the process moves to the decision state 230 to again determine if the current node is a leaf.

If a decision is made that the right child has been designed at the decision state 280 then the process 200 moves to a state 285 to evaluate the ensemble defect of the current parental node.

Subsequence Merging and Reoptimization

Thus, once the leaves of a selected node have been optimized, they are merged at a state 285 so that the merged sequence can be analyzed for conformance with the target structure. As subsequences are merged moving up the tree, each parent node can call the subsequence merging and reoptimization module 130 to initiate defect-weighted child sampling and reoptimization within its sub-tree if there are emergent defects resulting from crosstalk between child subsequences.

Thus, after evaluation of the ensemble defect of the parental node at the state 285, the process 200 moves to a decision state 290 to determine if the merge sequences from the leaf nodes satisfy a stop condition. If a decision is made that the merged sequence does not satisfy a stop condition, then the process moves to a state 295 to perform defect-weighted child sampling and re-optimization. After reaching the leave by recursively performing defect-weighted child sampling, the process 200 then returns to the state 235 to perform leaf optimization. The merging and reoptimization begins again at the termination of the leaf optimization.

Leaf reoptimization at state 235 starts from a new random initial test nucleotide sequence. After sibling nodes $k_l$ and $k_r$ have been optimized, parent node k may merge their native subsequences (setting $\phi_l^k = \phi_{native}^{k_l}$ and $\phi_r^k = \phi_{native}^{k_r}$) and evaluate $n^k$ to check for a parental stop condition:

$$n^k \leq \max(f_{stop} |s_l^k|, n_{native}^{k_l}) + \max(f_{stop} |s_r^k|, n_{native}^{k_r}).$$

For any node k with sequence $\phi^k$ and structure $s^k$, the ensemble defect, $n^k \equiv n(\phi^k, s^k)$, may be expressed as $$n^k = \sum_{1 \leq i \leq |s^k|} n_i^k,$$

-continued where $$n_i^k = 1 - \sum_{1 \leq j \leq |s^k|+1} P_{i,j}^k S_{i,j}^k.$$

is the contribution of nucleotide i to the ensemble defect of the node. For a parent node k, the ensemble defect can be expressed as a sum of contributions from bases partitioned to the left and right children $n^k = n_l^k + n_r^k$. For a child node $k_l$, the ensemble defect can be expressed as a sum of contributions from native and dummy nucleotides ($n^{k_l} = n_{native}^{k_l} + n_{dummy}^{k_l}$). Conceptually, $n_{native}^{k_l}$, the contribution of the native nucleotides to the ensemble defect of child $k_l$ (calculated on child node $k_l$ at cost $\Theta(|s^{k_l}|^3)$), approximates $n_l^k$, the contribution of the left-child nucleotides to the ensemble defect of parent k (calculated on parent node k at higher cost $\Theta(|s^k|^3)$). In general, $n_{native}^{k_l} \neq n_l^k$, because the dummy nucleotides in child node $k_l$ only approximate the influence of its sibling (which is fully accounted for only in the more expensive calculation on parent node k).

Failure to satisfy the stop condition at decision state 290 implies the existence of emergent defects resulting from crosstalk between the two child sequences. In this case, parent node k initiates defect-weighted child sampling and reoptimization within its subtree. Left child $k_l$ is selected for reoptimization with probability $n_l^k/n^k$ and right child $k_r$ is selected for reoptimization with probability $n_r^k/n^k$. This defect-weighted child sampling procedure is performed recursively until a leaf is encountered (each time using partitioned defect information inherited from the parent k that initiated the reoptimization). The standard leaf optimization procedure is then performed starting from a new random initial sequence. The use of random initial conditions during leaf reoptimization is based on the assumption that sequence space is sufficiently rich that emergent defects can typically be eliminated simply by designing a different leaf sequence. Following leaf reoptimization, merging begins again starting with the reoptimized leaf and its sibling. The elimination of emergent defects in parent k by defect-weighted child sampling and reoptimization is attempted up to $M_{reopt}$ times.

If this stop condition is satisfied, the process 200 moves to a state 320 to determine if the last node in the binary tree has been analyzed. This allows the subsequence merging to continue up the tree. If the last node in the tree has not been analyzed, the process 200 moves to a state 315 wherein the nucleotide sequence at the next node up or across the tree is selected for design or processing. The process 200 then returns to state 275 to determine if the nucleotide sequence at the left child node has been designed. If the last node has been analyzed, then the process 200 stops at an end state 325.

The utility of hierarchical structure decomposition reflects the assumption that sequence space is sufficiently rich that two subsequences optimized for sibling substructures will often not exhibit crosstalk when merged by a parent node. This hierarchical mutation procedure is designed to benefit from this property when it holds true, and to eliminate emergent defects when they do arise.

One embodiment of this entire design process is detailed in pseudocode shown in FIG. 3. As shown in the pseudocode of FIG. 4, for a given target structure s, a designed sequence φ is returned by the function call DESIGNSEQ(Ø, s, Ø, 1). During the recursive design procedure, φ, s, and n are local variables that are used to push sequence, structure, and defect information between nodes in the tree. By contrast, $n^{k,a}$ provides global storage for the ensemble defect of each node k. For a given k, the index, a=1, . . . , DEPTH(k), enables storage of the ensemble defect corresponding to the sequence for node k that has been accepted up to depth a in the tree. Storage of these historical values eliminates unnecessary recalculation of ensemble defects during subtree reoptimization.

Optimality Bound and Time Complexity

This hierarchical sequence design approach implies an asymptotic optimality bound on the cost of designing the full sequence relative to the cost of evaluating a single candidate mutation on the full sequence. For a target structure with N nucleotides, evaluation of a candidate sequence requires calculation of n(φ, s) at cost $c_{eval}(N) = \Theta(N^3)$. Performing sequence design using hierarchical structure decomposition, mutations are evaluated at the leaf nodes and merged subsequences are evaluated at all other nodes. For node k, the evaluation cost is $c_{eval}(|s_k|)$. If at least one mutation is required in each leaf, the design cost is minimized by maximizing the depth of the binary tree. Furthermore, at each depth in the tree, the design cost is minimized by balancing the tree. Hence, a lower bound on the cost of designing the full sequence is given by $$c_{des}(N) \geq c_{eval}(N)[1 + 2(\tfrac{1}{2})^3 + 4(\tfrac{1}{4})^3 + 8(\tfrac{1}{8})^3 + \ldots]$$

or $$c_{des}(N) \geq 4/3 \, c_{eval}(N).$$

Hence, if the sequence design process performs optimally for large N, we would expect the cost of full sequence design to be 4/3 the cost of evaluating a single mutation on the full sequence. In practice, many factors might be expected to undermine optimality: imperfect balancing of the tree, the addition of dummy nucleotides in each non-root node, the use of finite tree depth, leaf optimizations requiring evaluation of multiple candidate mutations, and reoptimization to eliminate emergent defects. This optimality bound implies time complexity $\Omega(N^3)$ for the sequence design process.

The systems and processes described above relate to a single-objective sequence design where the goal was to design the sequence of one or more interacting nucleic acid strands intended to adopt a target secondary structure at equilibrium. Thus, the sequence design was formulated as an optimization problem with the objective of reducing the ensemble defect below a user-specified stop condition. For a candidate sequence, φ, and a target secondary structure, s, the ensemble defect, n(φ; s), is the average number of incorrectly paired nucleotides at equilibrium evaluated over ensemble Γ. As described above, for a target secondary structure with N nucleotides, the above process seeks to satisfy $$n(\phi,s) \leq f^{stop} N$$

with $f^{stop} = 0.01$.

A single-objective design job is specified by entering a target secondary structure into the nucleic acid sequence design system 110 (FIG. 1). In one embodiment, the structure is entered into the system using dotparens-plus notation, each unpaired base is represented by a dot, each base pair by matching parentheses, and each nick between strands by a plus.

Target Structure Test Sets

Figure 5A:
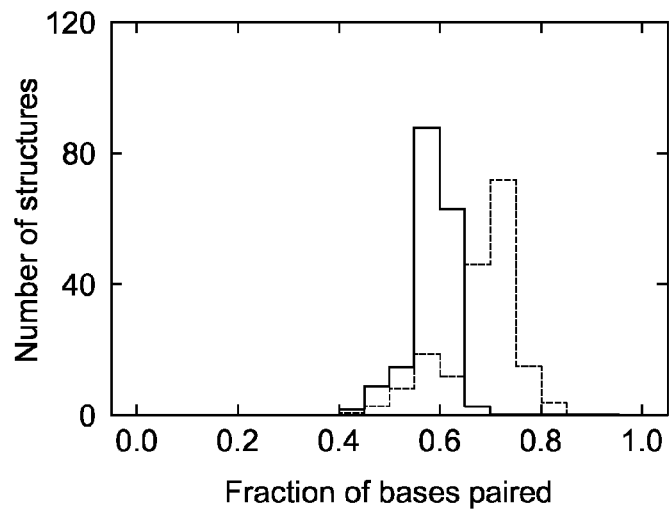
FIGS. 5a-5c are plots of the structural features of test sets generated to characterize the nucleic acid design system.
Figure 5B:
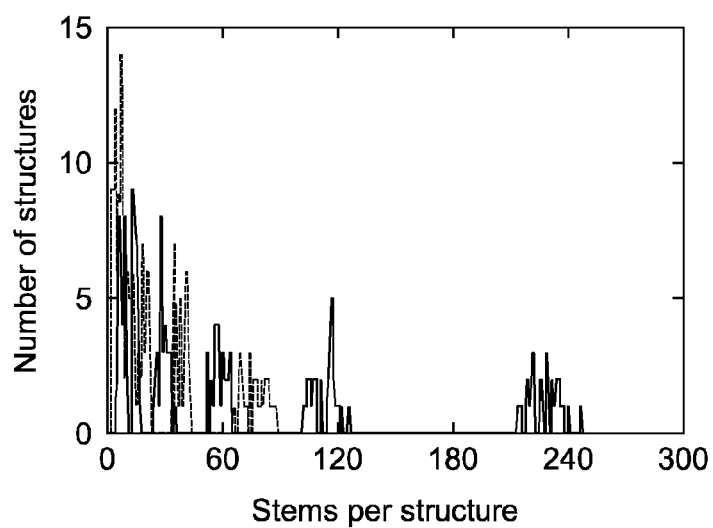
Figure 5C:
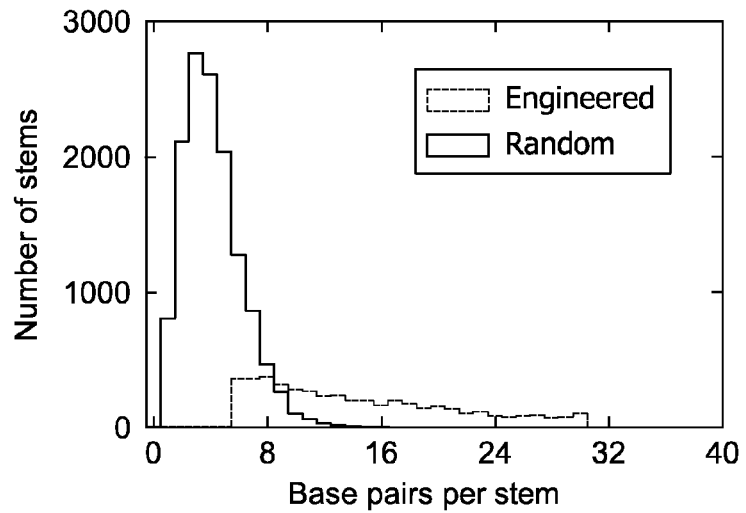

Process performance was evaluated on structure test sets containing 30 target structures for each of N∈{100, 200, 400, 800, 1600, 3200}. An engineered test set was generated by randomly selecting structural components and dimensions from ranges intended to reflect current practice in engineering nucleic acid secondary structures. A multi-stranded version was produced by introducing nicks into the structures in the engineered test set. Each structure in a random test set was obtained by calculating an MFE structure of a different random RNA sequence at 37° C. FIG. 5 compares the structural features of the engineered and random test sets. In general, the random test set has target structures with a lower fraction of bases paired, more duplex stems, and shorter duplex stems (as short as one base pair).

Other Processes

To illustrate the roles of hierarchical structure decomposition and defect-weighted sampling in the context of ensemble defect optimization, we compared our process to three alternative processes lacking either or both of these features:

Single-scale ensemble defect optimization with uniform mutation sampling. The leaf optimization process is applied directly on the full sequence using uniform mutation sampling in which each candidate mutation position is selected with equal probability.

Single-scale ensemble defect optimization with defect-weighted mutation sampling. The leaf optimization process is applied directly on the full sequence.

Hierarchical ensemble defect optimization with uniform mutation sampling. The hierarchical process is applied using uniform mutation sampling during leaf optimization and uniform child sampling during subsequence merging and reoptimization.

We also modified our process to compare performance to processes already known by others:

Single-scale probability defect optimization with uniform mutation sampling. This method seeks to design a sequence such that the probability defect satisfies the stop condition $\pi(\phi, s) \leq f_{stop}$. Satisfaction of this stop condition is sufficient to ensure that stop conditions $n(\phi, s) \leq f_{stop}N$ and $\mu(\phi, s) \leq f_{stop}N$ are also satisfied. Optimization is performed using a modified version of the leaf optimization process (with $\pi(\phi, s)$ taking the role of $n(\phi, s)$) applied directly on the full sequence using uniform mutation sampling.

Hierarchical MFE defect optimization with weighted mutation sampling. This method seeks to design a sequence such that the MFE defect satisfies the stop condition $\mu(\phi, s) \leq f_{stop}N$. Optimization is performed using a modified version of our process with $\mu^k$ taking the role of $n^k$.

The sequence design process was coded in the C programming language. By parallelizing the dynamic program for evaluating $P(\phi)$ using MPI,[26] the sequence design process reduced run time using multiple cores. For a design job allocated M computational cores, each evaluation of $P^k$ for node k with structure $s^k$ is performed using m cores for some $m \in 1, \ldots, M$ selected to approximately minimize run time based on $|s^k|$.

Results

Our primary test scenario was RNA sequence design at 37° C. for target structures in the engineered test set. For each target structure in a test set, 10 independent design trials were performed. Each plotted data point represents a median over 300 design trials (10 trials for each of 30 structures for a given size N).

Process Performance and Asymptotic Optimality

Figures 6A, 6B:
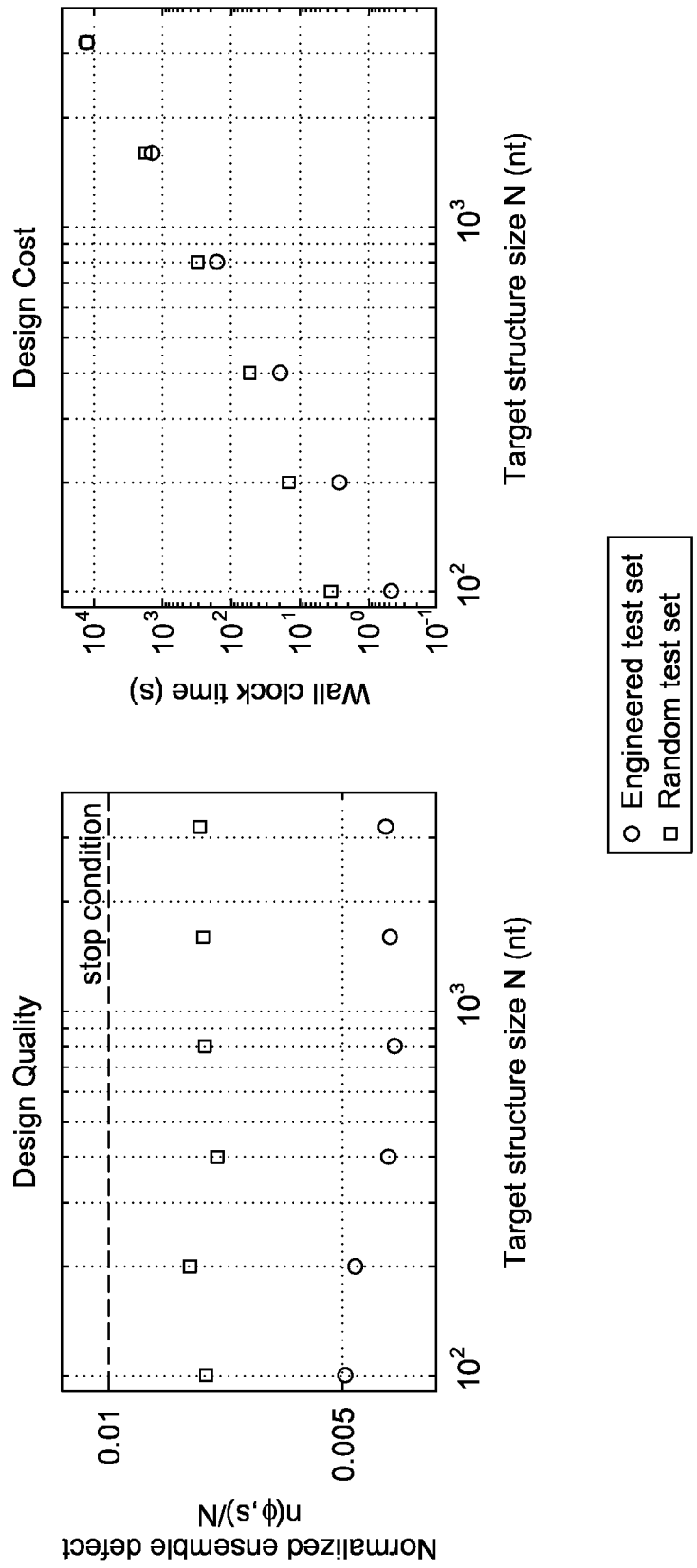

FIG. 6 demonstrates the typical performance of our process across a range of values of N using the engineered and random test sets. Typical designs surpassed the desired design quality ($n(\phi, s) \leq N/100$) as a result of overshooting stop conditions lower in the decomposition tree (FIG. 6a). For the engineered test set, typical design cost ranges from a fraction of a second for N=100 to roughly three hours for N=3200 (FIG. 6b). For small N, the design cost for the random test set is higher than for the engineered test set, becoming comparable as N increases. Typical GC content is less than 60% (starting from random initial sequences with ≈50% GC content; FIG. 6c). Remarkably, as the depth of the decomposition tree increased with N, the relative cost of design, $c_{des}(N)/c_{eval}(N)$, decreased asymptotically to the optimal bound of 4/3 (FIG. 6d). Hence, for sufficiently large N, the typical cost of sequence design is only 4/3 the cost of a single mutation evaluation on the root node. Mutation evaluation had time complexity $\Theta(N^3)$ and was empirically observed to be approximately in the asymptotic regime. Hence, for our design process, the empirical observation of asymptotic optimality demonstrates that the exponent in the $\Omega(N^3)$ time complexity bound is sharp.

Leaf Independence and Emergent Defects

FIG. 7 compares the ensemble defect evaluated at the root node, to the sum of the ensemble defects evaluated at the leaf nodes. If the assumption of leaf independence is valid (i.e., if dummy nucleotides are effective at mimicking parental environments and there is minimal crosstalk between merged subsequences), we would expect the data to fall near the diagonal.

For the engineered test set (FIG. 7a), we observed three striking properties. First, for random initial sequences, the assumption of leaf independence was well-justified despite the fact that the ensemble defect is large. Second, leaf optimization followed by merging without reoptimization (i.e., $M_{reopt}=0$) typically yielded full sequence designs that achieved the desired design quality ($n(\phi, s) \leq N/100$ on the root), with emergent defects arising only in a minority of cases. Third, these emergent defects were successfully eliminated by defect-weighted child sampling and reoptimization starting from new random initial subsequences. The resulting full sequence designs exhibited leaf independence and satisfied the stop condition.

By comparison, for the random test set, merging of leaf-optimized sequences typically did lead to emergent defects in the root node. Even in this case, our process was found to successfully eliminate emergent defects using defect-weighted child sampling and reoptimization starting from new random initial subsequences.

Contributions of Processic Ingredients

Figure 8B:
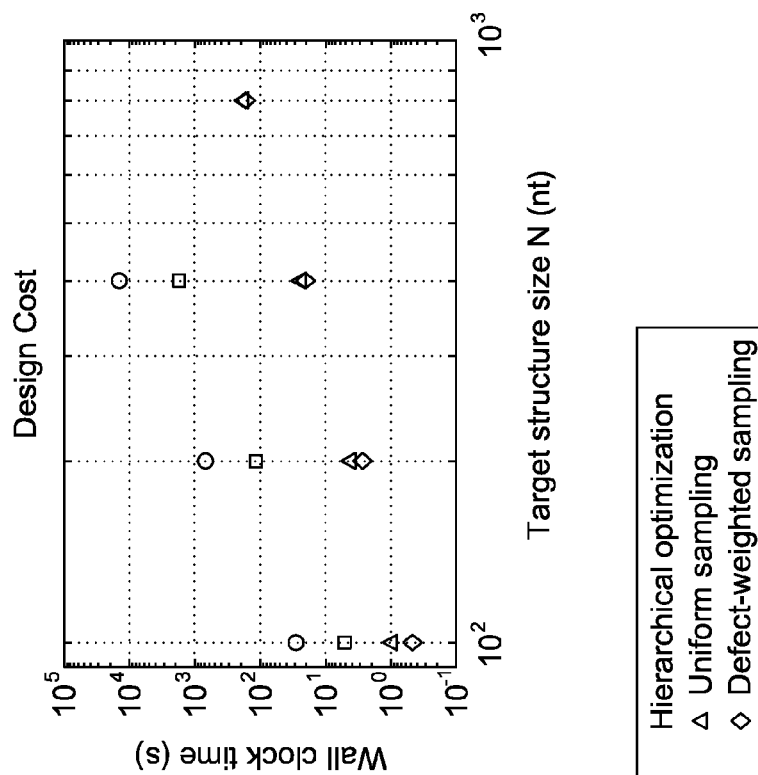
Figure 8A:
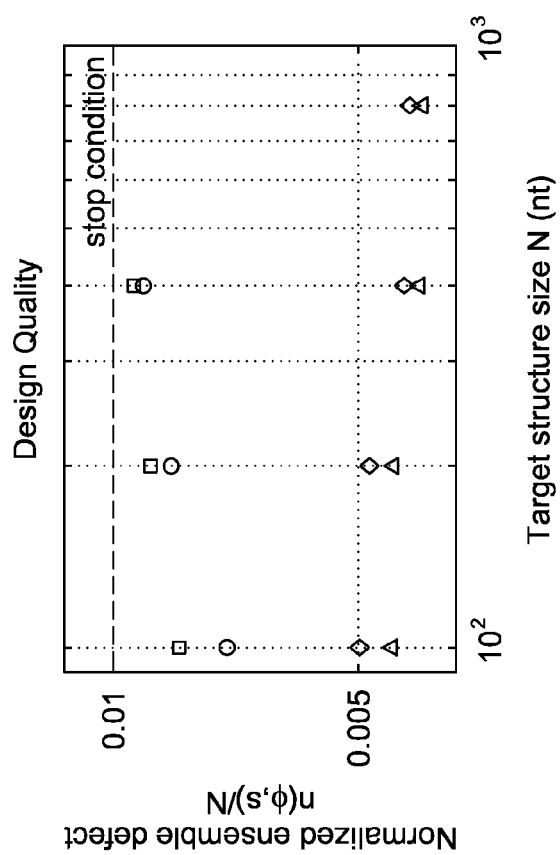

FIG. 8 shows the isolation of contributions of hierarchical structure decomposition and defect-weighted sampling to the ensemble defect optimization process by comparing performance to three modified processes lacking one or both ingredients. All four methods typically achieved the desired design quality, with hierarchical methods surpassing the quality requirement for the root node as a result of overshooting stop conditions lower in the decomposition tree. Hierarchical methods dramatically reduced design costs relative to their single-scale counterparts (which were not tested for N=800 due to high cost). Defect-weighted sampling reduced design cost and GC content by focusing mutation effort on the most defective subsequences. For the single-scale methods, the relative cost of design, $c_{des}(N)/c_{eval}(N)$, increases with N. For hierarchical methods, $c_{des}(N)/c_{eval}(N)$ decreases asymptotically to the optimal bound of 4/3 as N increases. Our process thus combined the design quality of ensemble defect optimization, the reduced cost and asymptotic optimality of hierarchical decomposition, and the reduced cost and reduced GC content of defect-weighted sampling.

Sequence Initialization

Figure 9A:
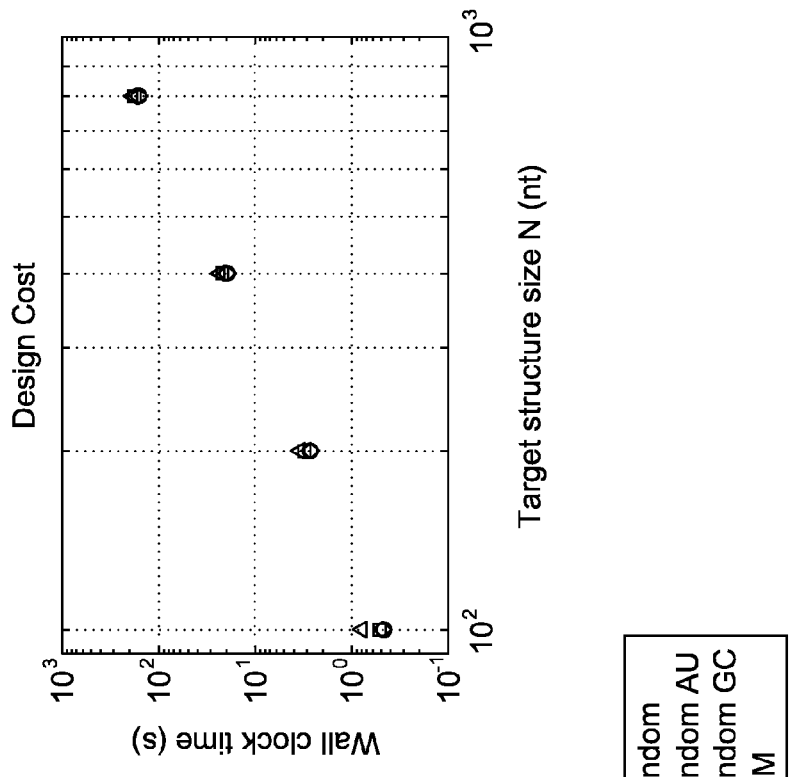
FIGS. 9a-9d show plots of the effects of sequence initialization on performance for certain of the embodiments. Particularly, four types of sequences are considered: entirely random sequences, sequences of random adenosine-uracil (AU), sequences of random guanine-cytosine (GC), and sequences satisfying sequence symmetry minimization (SSM).
Figure 9B:
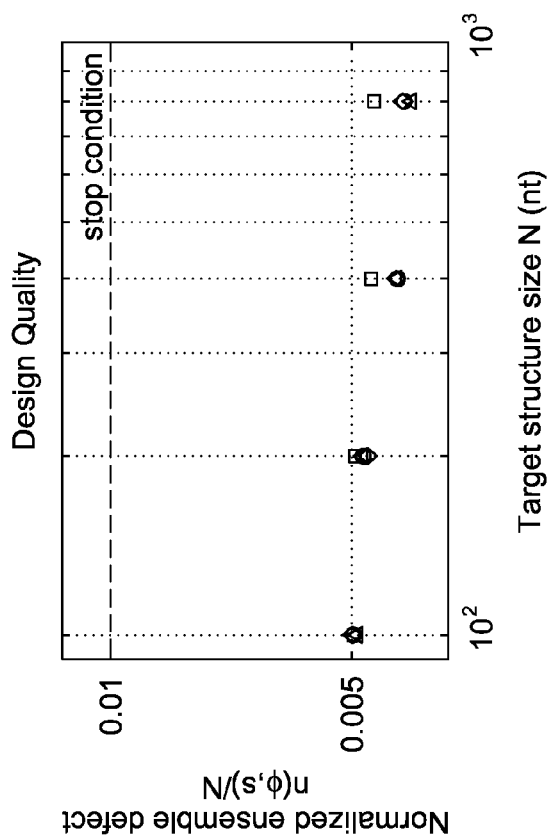
Figures 9C, 9D:
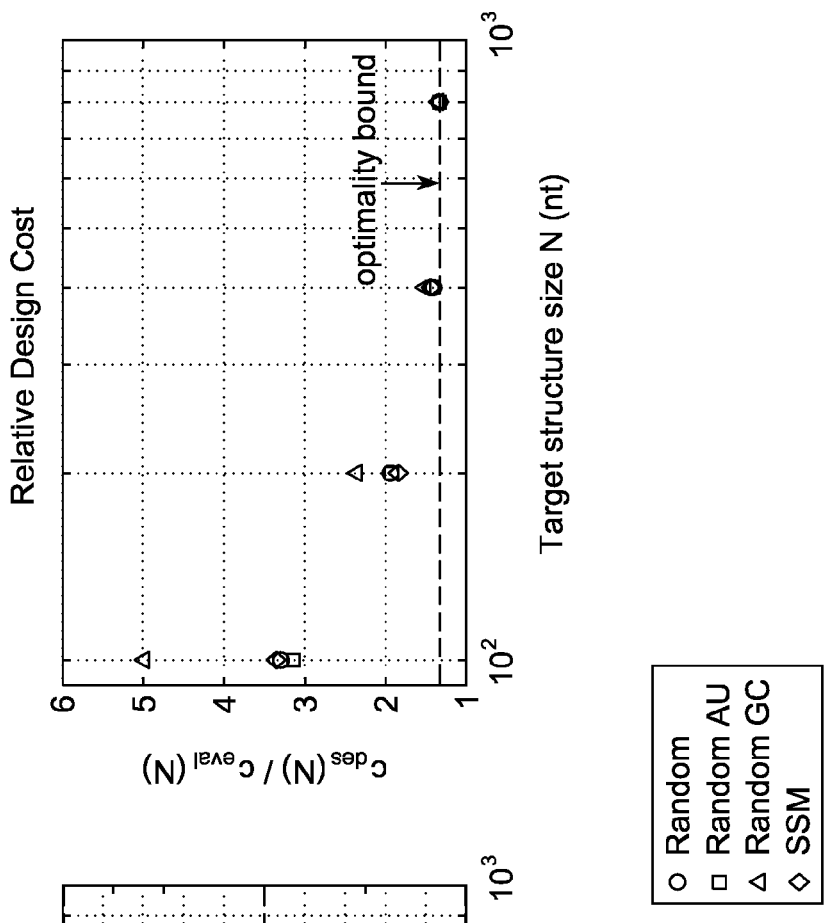

To explore the effect of sequence initialization on typical design quality and cost, we tested four types of initial conditions (FIG. 9): random sequences (default), random sequences using only A and T bases, random sequences using only G and C bases, and sequences satisfying sequence symmetry minimization (SSM). The desired design quality was achieved independent of the initial conditions (FIG. 9a), which had little effect on design cost (FIGS. 9b and 9d). Designs initiated with random AT sequences or with random GC sequences illustrated that the ensemble defect stop condition can be satisfied over a broad range of GC contents (FIG. 9c).

Stop Condition Stringency

Figure 10B:
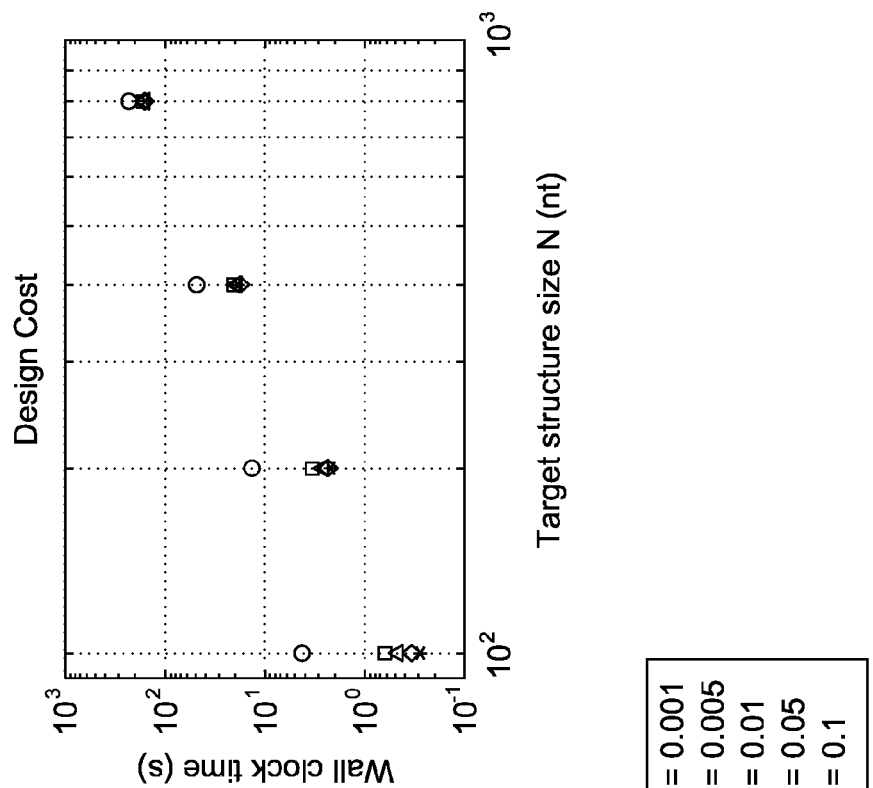
Figure 10A:
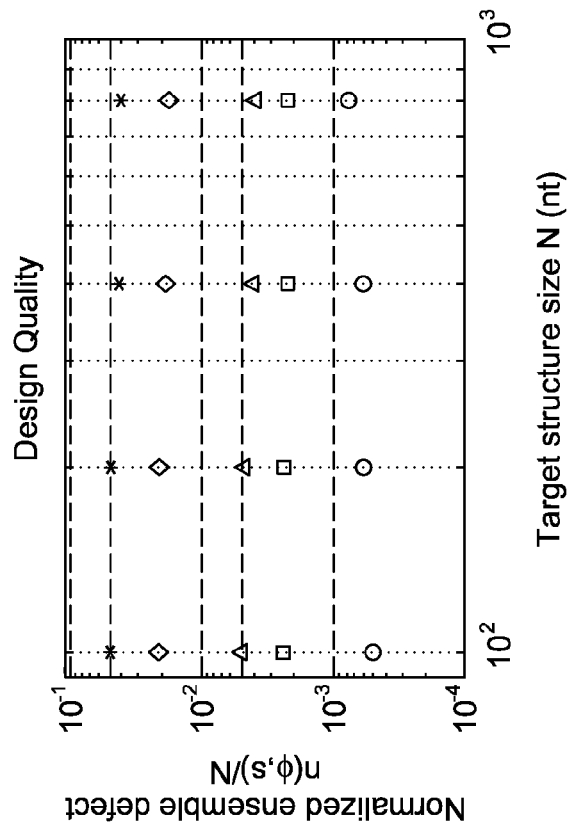

FIG. 10 depicts typical process performance for five different levels of stringency in the stop condition: $f_{stop} \in \{0.001, 0.005, 0.01(\text{default}), 0.05, 0.10\}$. For each stop condition, the observed design quality was better than required (resulting from overshooting stop conditions lower in the decomposition tree). Consistent with empirical asymptotic optimality, the design cost was independent of $f_{stop}$ for sufficiently large N (for the tested stringency levels). It is noteworthy that the process was found to be capable of routinely and efficiently designing sequences with ensemble defects of less than N/1000.

Multi-Stranded Target Structures

Figure 11B:
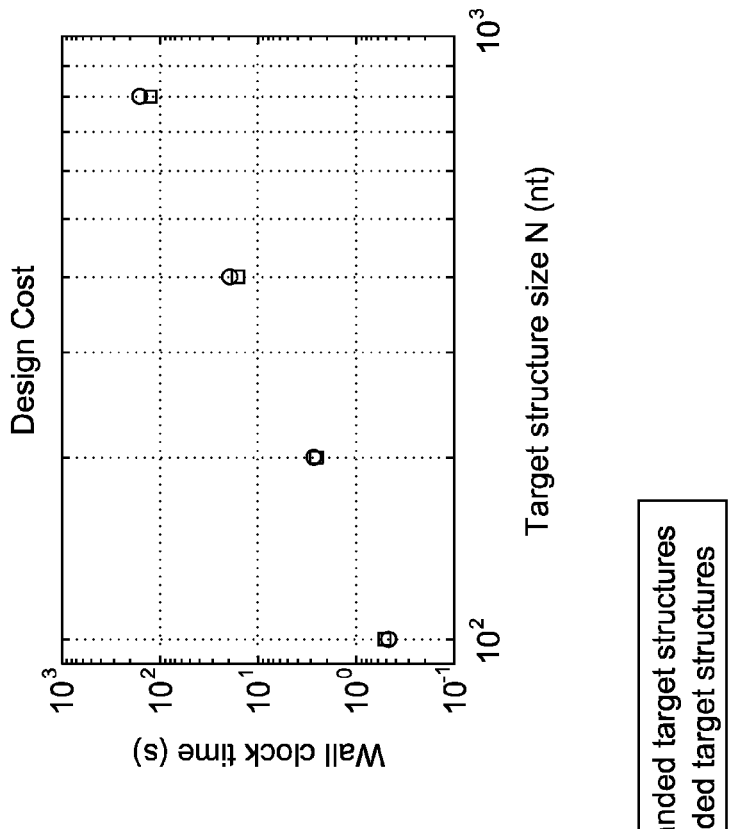
Figure 11A:
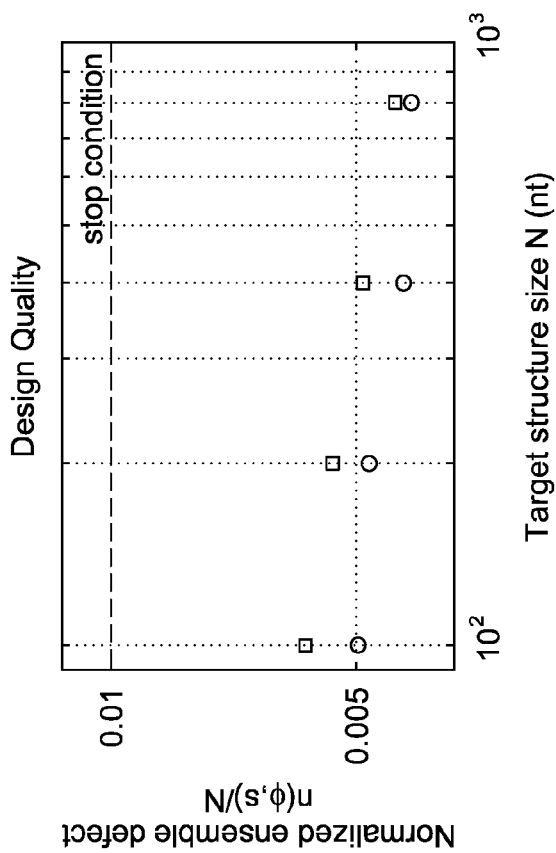

Multi-stranded target structures arise frequently in engineering practice. FIG. 11 demonstrated that our process performs similarly on a single-stranded or multi-stranded target structure.

Design Material

Figure 12A:
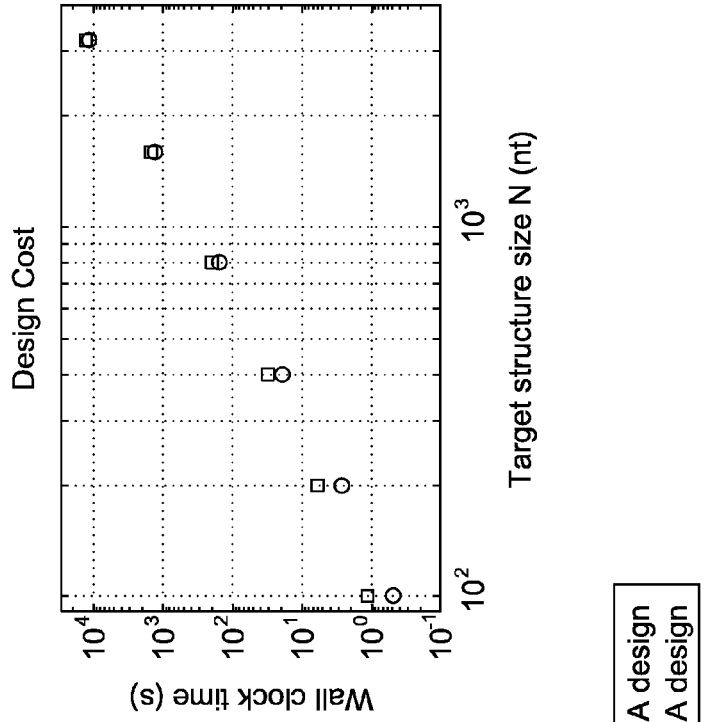
Figure 12B:
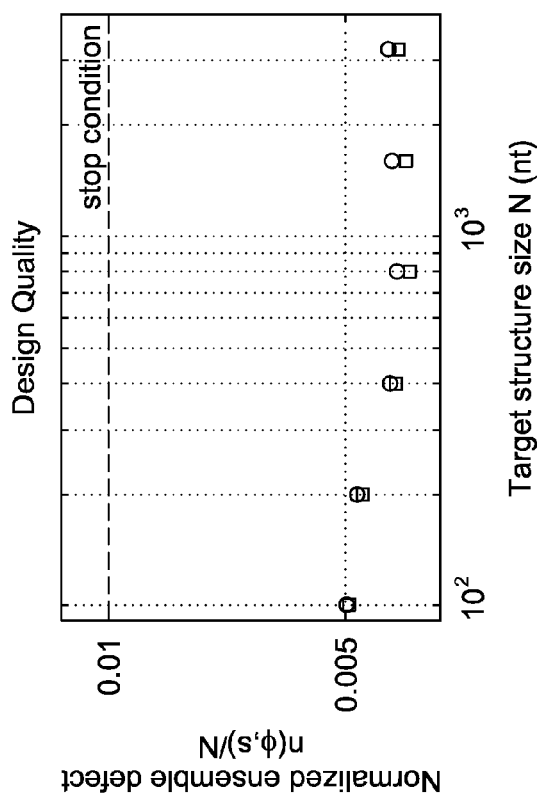

FIG. 12 compares RNA and DNA design. DNA designs are performed in 1 M Na$^+$ at 23° C. to reflect that DNA systems are typically engineered for room temperature studies. In comparison to RNA design, DNA design leads to similar design quality (FIG. 12a), higher design cost (FIG. 12b), and somewhat higher GC content (FIG. 12c), while continuing to exhibit asymptotic optimality (FIG. 12d).

Sequence Constraints and Pattern Prevention

Figure 13A:
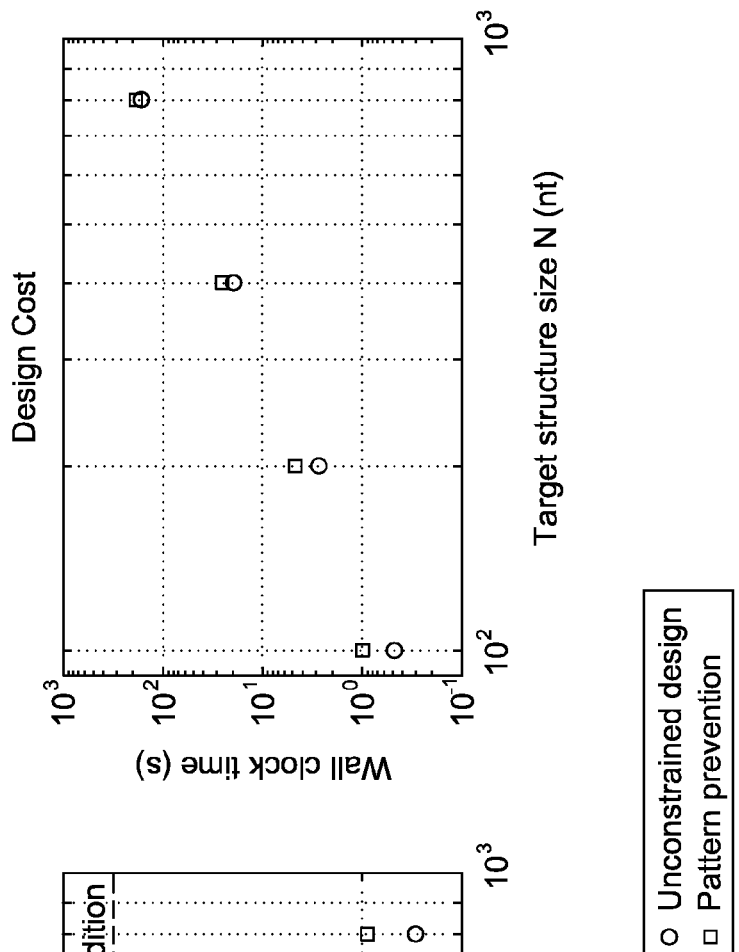
Figure 13B:
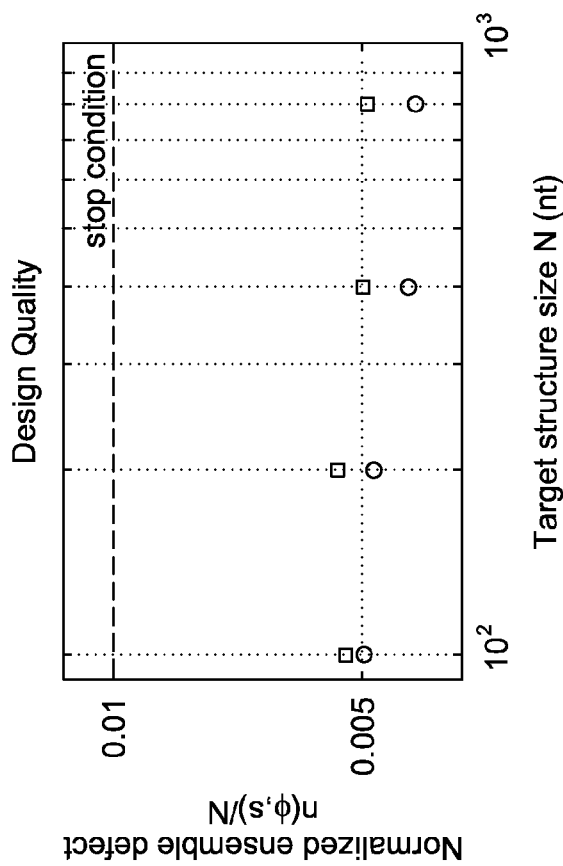

Molecular engineers sometimes constrain the sequence of certain nucleotides in the target structure (e.g., to ensure complementarity to a specific biological sequence), or prevent certain patterns from appearing anywhere in the design (e.g., GGGG). Our process accepts sequence constraints and pattern prevention requirements expressed using standard nucleic acid codes. FIG. 13 demonstrates that the prevention of patterns {AAAA, CCCC, GGGG, UUUU, KKKKKK, MMMMMM, RRRRRR, SSSSSS, WWWWWW, YYYYYY} had little effect on design quality or GC content (FIGS. 13a and 13c), and somewhat increases design cost while retaining asymptotic optimality (FIGS. 13b and 13d).

Parallel Efficiency and Speedup

Figure 14B:
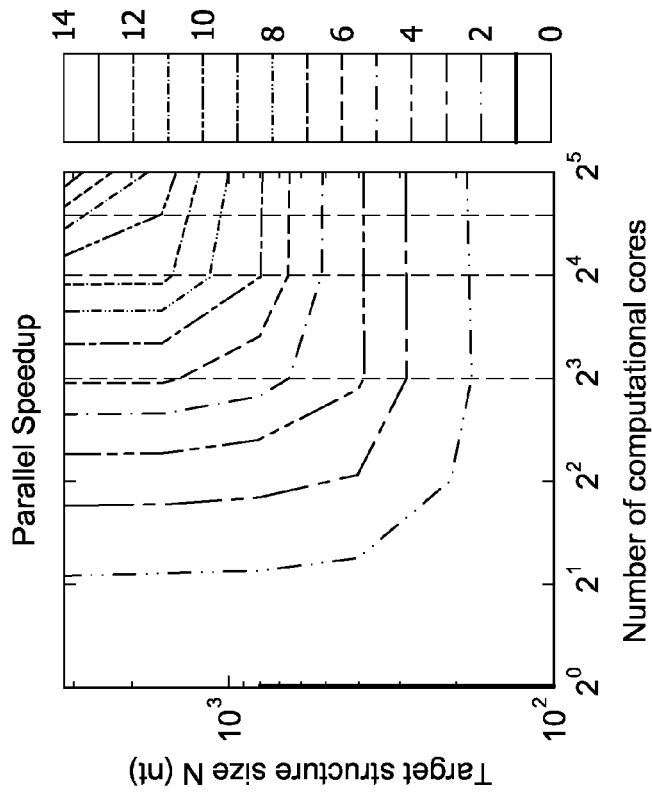
FIG. 14b plots the speedup when certain embodiments are parallelized.
Figure 14A:
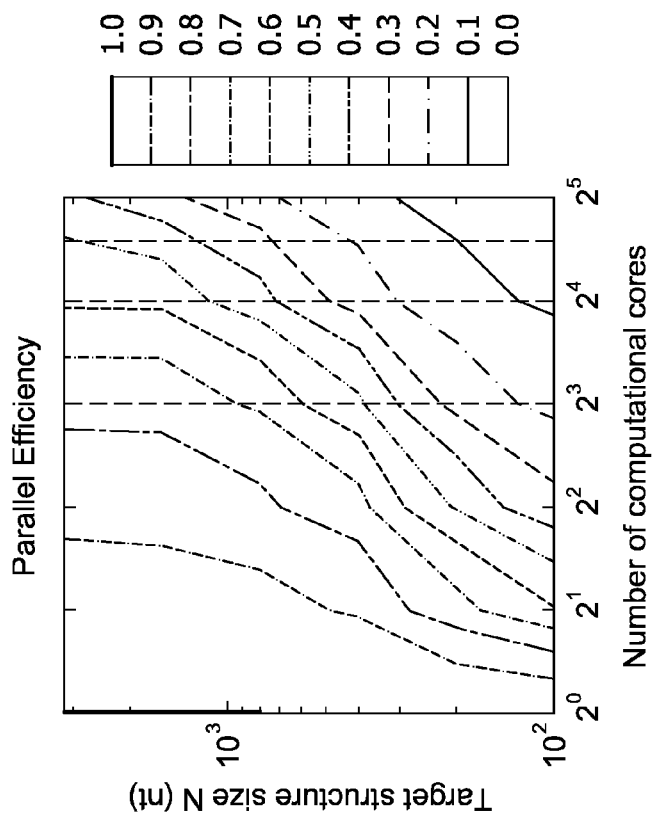
FIG. 14a plots the efficiency on engineered test structures when certain embodiments are parallelized.

The contour plots of FIG. 14 demonstrate the parallel efficiency and speedup achieved using a parallel implementation of the design process on M computational cores (efficiency (N, M)=t(N, 1)/(t(N, M)×M), speedup (N, M)=t(N, 1)/t(N, M), where t is wall clock time). Using two computational cores, the parallel efficiency exceeds ≈0.9 for target structures with N>400. Using 32 computational cores, the parallel speedup is ≈14 for target structures with N=3200.

Comparison to Previous Approaches

FIG. 15 compares the performance of the described process to the performance of processes discussed by others. Single-scale methods that employed uniform mutation sampling to optimize either ensemble defect or probability defect achieved the desired design quality at significantly higher cost and with significantly higher GC content (FIGS. 15a-c). Sequences resulting from probability defect optimization typically surpass the ensemble defect stop condition despite failing to satisfy the probability defect stop condition (FIG. 15e), reflecting the pessimism of $\pi(\phi, s)$ in characterizing the equilibrium structural defect over ensemble Γ. For either single-scale method, the relative cost of design, $c_{des}(N)/c_{eval}(N)$, increases with N (FIG. 15d). Owing to the high cost of the single-scale approaches, designs were not attempted for large N.

Figure 15A:
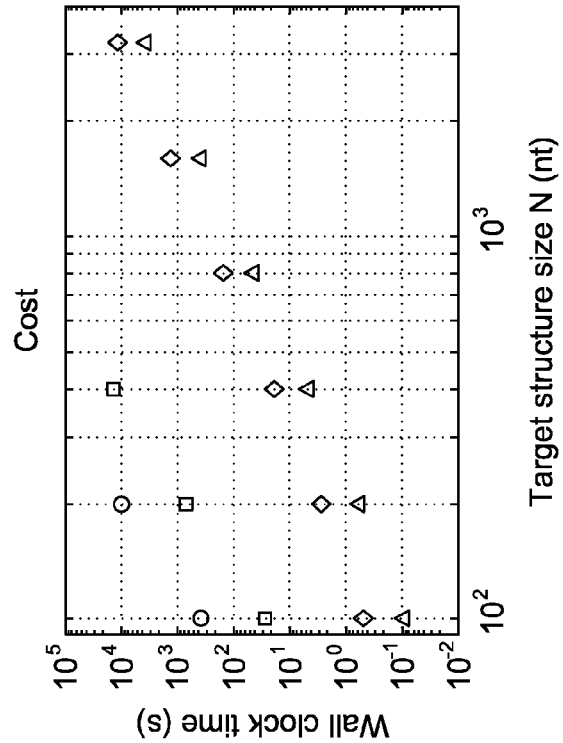
Figure 15B:
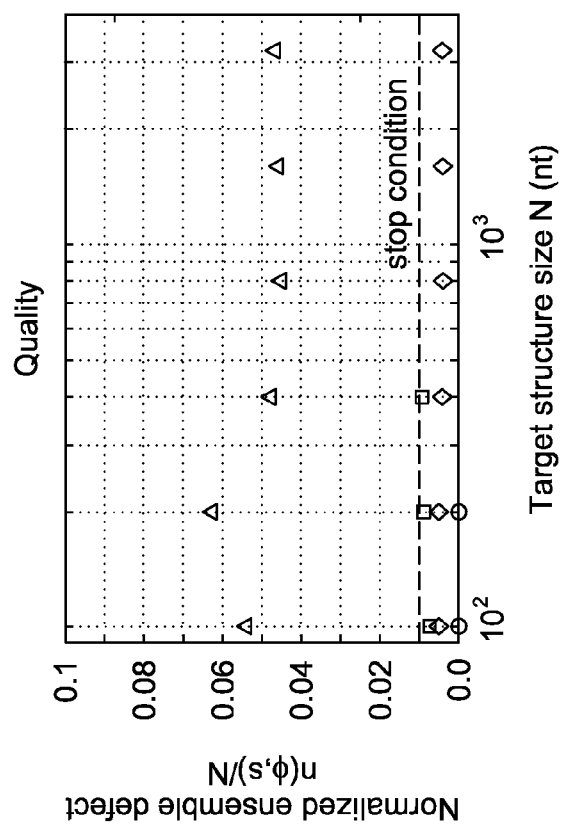
Figure 15D:
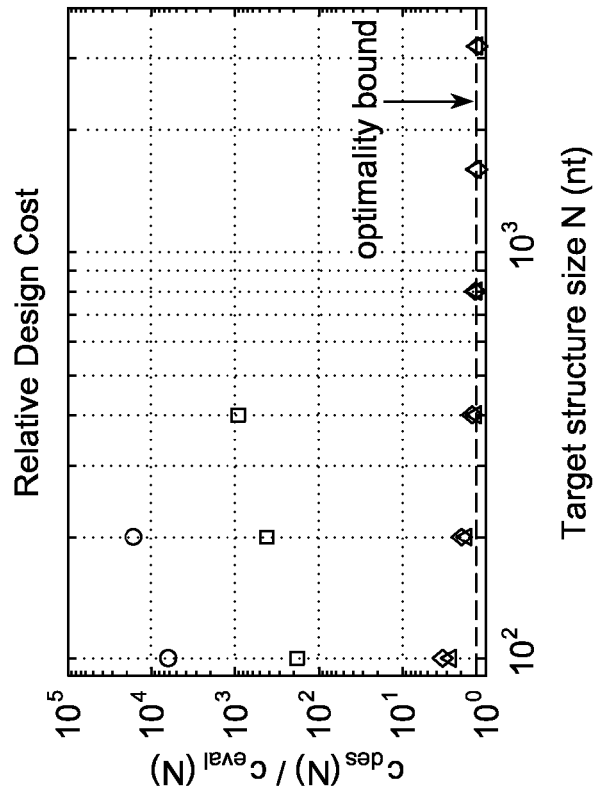
Figure 15C:
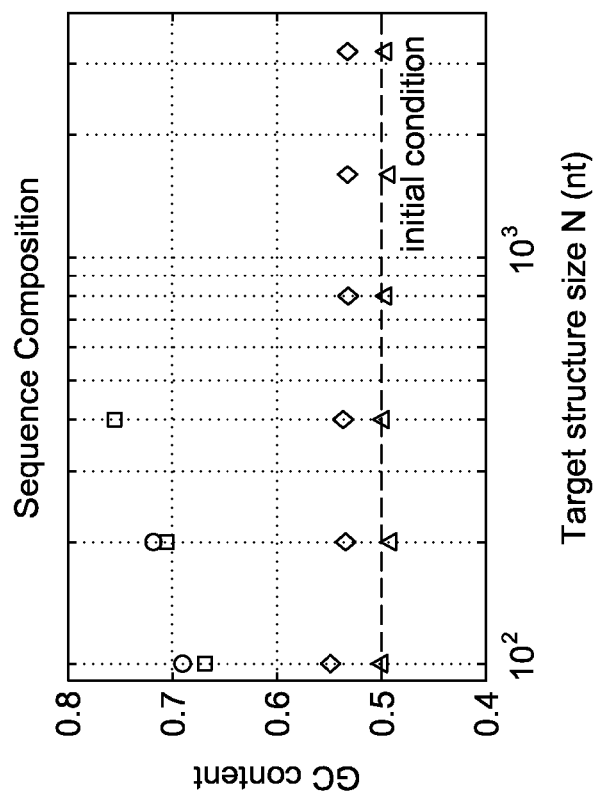

By contrast, hierarchical MFE defect optimization with defect-weighted sampling led to efficient satisfaction of the MFE stop condition (FIGS. 15b and 15f), exhibiting asymptotic optimality with $c_{des}(N)/c_{eval}(N)$ approaching 4/3 for large N (FIG. 15d). Asymptotically, the cost of hierarchical MFE optimization relative to hierarchical ensemble defect optimization is lower by a constant factor corresponding to the relative cost of evaluating the two objective functions using $\Theta(N^3)$ dynamic programs (FIGS. 15b and 15d). The shortcoming of MFE defect optimization is the unreliability of $s^{MFE}(\phi)$ in characterizing the equilibrium structural properties of ensemble Γ. Despite satisfying the MFE defect stop condition, sequences designed via MFE defect optimization typically fail to achieve the ensemble defect stop condition by roughly a factor of five for the engineered test set (FIG. 15a), and by roughly a factor of 20 for the random test set.

SUMMARY OF RESULTS

Using a $\Theta(N^3)$ dynamic program to evaluate the design objective function, we derived an asymptotic optimality bound on design time: for large N, the minimum cost to design a sequence with N nucleotides was 4/3 the cost of evaluating the objective function once on N nucleotides. Hence, our design process has time complexity $\Omega(N^3)$.

We studied the performance of our process in the context of empirical secondary structure free energy models that have practical utility for the analysis and design of functional nucleic acid systems. In particular, we examined RNA design at 37° C. on target structures containing N∈{100, 200, 400, 800, 1600, 3200} nucleotides and duplex stems ranging from 1 to 30 base pairs. Empirically, we observe several striking properties. For example, emergent defects were sufficiently infrequent that they were typically eliminated by leaf reoptimization starting from new random initial sequences. In addition, it was routine to design sequences with ensemble defect $n(\phi, s)<N/100$ over a wide range of GC contents. Additionally, the process described herein exhibited asymptotic optimality for large N, with full sequence design costing roughly 4/3 the cost of a single evaluation of the objective function. Hence, the process was efficient in the sense that the exponent in the $\Omega(N^3)$ time complexity bound is sharp.

While the above processes and methods are described above as including certain steps and are described in a particular order, it should be recognized that these processes and methods may include additional steps or may omit some of the steps described. Further, each of the steps of the processes does not necessarily need to be performed in the order it is described.

While the above description has shown, described, and pointed out novel features of the invention as applied to various embodiments, it will be understood that various omissions, substitutions, and changes in the form and details of the system or process illustrated may be made by those skilled in the art without departing from the spirit of the invention. As will be recognized, the present invention may be embodied within a form that does not provide all of the features and benefits set forth herein, as some features may be used or practiced separately from others.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

mutation sampling so that a candidate mutation position of a nucleotide in the nucleotide sequence is randomly selected with a probability proportional to the ensemble defect contribution of the nucleotide.

4. The electronic system of claim 1, wherein the code configured to recurse the nodes of the tree and merge the determined leaf nucleotide sequences identifies defective subtrees of the tree during a merger process and re-optimizes any defective subtree by defect-weighted child sampling, wherein a child node is randomly selected for re-optimization with a probability that is proportional to the ensemble defect contribution of the child node.

What is claimed is:

1. An electronic system having one or more processors and configured for optimizing a sequence of a nucleic acid strand to adopt a specific target secondary structure at equilibrium, comprising:
an input for receiving a target secondary structure;
code running on a processor and configured to decompose the target secondary structure at split points into a tree of parental nodes, child nodes and leaf nodes wherein each split point is formed within a duplex stem of the target structure;
code running on a processor and configured to determine a leaf nucleotide sequence of the target structure at each leaf node in the tree; and
code running on a processor and configured to recurse the nodes of the tree and merge the determined leaf nucleotide sequences at each node to optimize the nucleotide sequence of a nucleic acid strand that adopts the specific target secondary structure at equilibrium.

2. The electronic system of claim 1, wherein the code configured to determine a leaf nucleotide sequence is configured to optimize the nucleotide sequence of the leaf nodes of the tree to reduce an ensemble defect of each leaf node below a user-specified stop condition.

3. The electronic system of claim 2, wherein the code configured to determine a leaf nucleotide sequence is configured to optimize the ensemble defect using defect weighted 5. The electronic system of claim 1, wherein the code configured to decompose the target secondary structure is configured to add dummy nucleotides to the split points of the tree.

6. The electronic system of claim 5, wherein the code configured to recurse the nodes of the tree and merge the determined leaf nucleotide sequences is configured to remove the dummy nucleotides when merging the leaves into parent nodes.

7. The electronic system of claim 1, wherein the code configured to determine a leaf nucleotide sequence is configured to select an initial random nucleotide sequence to be compared against the decomposed target structure at each leaf node in the tree.

8. The electronic system of claim 1, wherein the tree is a binary tree.

9. The electronic system of claim 1, wherein the system comprises computer servers.

10. The electronic system of claim 7, wherein the code configured to determine a leaf nucleotide sequence is configured to iteratively mutate nucleotides of the initial random nucleic acid sequence to optimize the nucleotide sequence at each leaf of the tree.

11. The electronic system of claim 1, wherein the specific target secondary structure comprises one or more nucleic acid chains.

12. The electronic system of claim 1, wherein the system is configured to convert the received target secondary structure to a matrix.

13. The electronic system of claim 1, wherein the code configured to decompose the target secondary structure identifies stem structures within the target structure.

14. The electronic system of claim 1, wherein the code configured to decompose the target secondary structure decomposes the parental nodes until all the nodes are leaf nodes.

15. The electronic system of claim 1, wherein a nucleotide sequence of a nucleic acid strand that adopts the target secondary structure is provided when the code configured to recurse the nodes of the tree and merge the determined leaf nucleotide sequences identifies a root node.

16. An electronic system comprising one or more processors configured for optimizing a sequence of a polynucleotide strand to adopt a specific target secondary structure at equilibrium, comprising:
   an input for receiving a target secondary structure;
   means running on a processor for decomposing the target secondary structure at split points into a tree of parental nodes, child nodes and leaf nodes wherein each split point is formed within a duplex stem of the target structure;
   means running on a processor for determining a leaf nucleotide sequence of the target structure at each leaf node in the tree; and
   means running on a processor for recursing the nodes of the tree and merge the determined leaf nucleotide sequences at each node to optimize the nucleotide sequence of a nucleic acid strand that adopts the specific target secondary structure at equilibrium.

17. The electronic system of claim 16, comprising a processor configured to run instructions provided by code configured to decompose the target secondary structure.

18. The electronic system of claim 16, comprising a processor configured to run instructions provided by code configured to determine a leaf nucleotide sequence.

19. The electronic system of claim 16, comprising a processor configured to run instructions provided by a code configured to recurse the nodes of the tree.

20. The electronic system of claim 16, comprising a memory for storing a nucleotide sequence that is optimized for the nucleic acid strand.

21. An electronic system comprising one or more processors configured for optimizing a sequence of a polynucleotide strand to adopt a specific target secondary structure at equilibrium, comprising:
   an input for receiving a target secondary structure;
   one or more processors configured to perform a method comprising:
      decomposing the target secondary structure at split points into a tree of parental nodes, child nodes and leaf nodes wherein each split point is formed within a duplex stem of the target structure;
      determining a leaf nucleotide sequence of the target structure at each leaf node in the tree; and
      recursing the nodes of the tree and merge the determined leaf nucleotide sequences at each node to optimize the nucleotide sequence of a nucleic acid strand that adopts the specific target secondary structure at equilibrium.

* * * * *